(12) United States Patent
Lee et al.

(10) Patent No.: US 11,911,485 B2
(45) Date of Patent: *Feb. 27, 2024

(54) IONIZABLE LIPID COMPOUNDS, LIPID NANOPARTICLES COMPRISING SAME AND THERAPEUTIC USES THEREOF

(71) Applicant: EnhancedBio Inc., Seoul (KR)

(72) Inventors: Hyukjin Lee, Seoul (KR); Minjeong Kim, Seoul (KR); Hansaem Jeong, Daejeon (KR); Hyokyoung Kwon, Seoul (KR); Yunmi Seo, Seoul (KR); Michaela Jeong, Seoul (KR)

(73) Assignee: EnhancedBio Inc., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/816,427

(22) Filed: Aug. 1, 2022

(65) Prior Publication Data

US 2023/0310644 A1    Oct. 5, 2023

Related U.S. Application Data

(63) Continuation of application No. 17/504,785, filed on Oct. 19, 2021, now Pat. No. 11,464,870, which is a continuation of application No. PCT/KR2020/019502, filed on Dec. 31, 2020.

(30) Foreign Application Priority Data

Jan. 15, 2020 (KR) .................. 10-2020-0005642
Apr. 2, 2020 (KR) .................. 10-2020-0040586

(51) Int. Cl.
| | |
|---|---|
| *A61K 47/69* | (2017.01) |
| *A61K 31/7105* | (2006.01) |
| *A61K 31/711* | (2006.01) |
| *A61K 47/22* | (2006.01) |
| *A61K 47/24* | (2006.01) |
| *A61K 47/28* | (2006.01) |
| *A61K 48/00* | (2006.01) |

(52) U.S. Cl.
CPC ...... *A61K 47/6909* (2017.08); *A61K 31/7105* (2013.01); *A61K 31/711* (2013.01); *A61K 47/22* (2013.01); *A61K 47/24* (2013.01); *A61K 47/28* (2013.01); *A61K 48/00* (2013.01)

(58) Field of Classification Search
CPC .................................................. A61K 47/6909
See application file for complete search history.

(56) References Cited

FOREIGN PATENT DOCUMENTS

WO    WO-2019110067 A1 *   6/2019

* cited by examiner

*Primary Examiner* — Benjamin J Packard
(74) *Attorney, Agent, or Firm* — United One Law Group LLC; Kongsik Kim; Jhongwoo Peck

(57) ABSTRACT

The present invention relates to lipid nanoparticles for in vivo drug delivery and uses thereof, and the lipid nanoparticle are liver tissue-specific, have excellent biocompatibility and can deliver a gene therapeutic agent with high efficiency, and thus it can be usefully used in related technical fields such as lipid nanoparticle mediated gene therapy.

19 Claims, 7 Drawing Sheets

Specification includes a Sequence Listing.

IONIZABLE LIPID COMPOUNDS, LIPID NANOPARTICLES COMPRISING SAME AND THERAPEUTIC USES THEREOF

CROSS-REFERENCE TO RELATED APPLICATIONS

This application is a continuation of U.S. application Ser. No. 17/504,785 filed on Oct. 19, 2021, which is a national phase of International Application No. PCT/KR2020/019502 filed on Dec. 31, 2020, which claims priority to Korean Application No. 10-2020-0040586 filed on Apr. 2, 2020 and Korean Application No. 10-2020-0005642 filed on Jan. 15, 2020, which applications are incorporated herein by reference.

SEQUENCE LISTING

The present application contains a Sequence Listing which has been submitted electronically in ASCII format and is hereby incorporated by reference in its entirety. The ASCII copy, created on Nov. 17, 2022, is named ENC-P30001C.xml and is 26,096 bytes in size.

TECHNICAL FIELD

The present invention relates to lipid nanoparticles for in vivo drug delivery and uses thereof.

BACKGROUND ART

In the pharmaceutical formulation industry, the drug delivery system (DDS), designed to efficiently deliver the required amount of the drug by reducing side effects of the drug and maximizing efficacy and effects, is a high value-added core technology which can create economic benefits comparable to that of new drug development and has great potential for success and its purpose is to improve the quality of patient treatment by making drug administration more efficient.

The solubilization technology of poorly soluble drugs belonging to the drug absorption promotion technology, which is one of the core technologies of the drug delivery system, is considered the most reasonable way to reduce the development cost of new drug substances and at the same time increase the added value of currently marketed drugs. In particular, the development of improved new drugs through the development of drug solubilization technology in a situation where new drug development conditions are poor as in Korea is a field that can create enormous added value at a low cost.

Gene therapy using a genetic drug delivery system is established in a large hope of modifying genetic binding and to treat numerous diseases. In the successful and securely performing this gene therapy, the effective gene delivery is one of the main challenges and the virus delivery system was proved to be effective in gene delivery. However, due to some defects such as immunogenicity, limitation of the inserted DNA size and difficulties of mass production, the use of viruses are limited as a gene delivery system. Non-viral gene carriers such as cationic liposome and polymers began to be noted as an alternative means of a viral system.

Improved stability profile and ease of manufacturing and operation of the polymer delivery system triggered studies on the design and synthesis of a non-toxic and biodegradable polymer carrier for effective and safe gene delivery. Poly (L-lysine), polyethylenimine, starburst, polyamidoamine dendrimer, and cationic liposome voluntarily, and the like can be self-assembled and compress plasmid DNA (pDNA) into a small structure sufficiently to enter cells through endocytosis, and therefore they have been widely studied as a non-viral gene delivery system.

Nucleic acids such as antisense RNA, siRNA, and the like are a material capable of inhibiting expression of specific proteins in vivo, and are spotlighted as an important tool for treatment of cancer, genetic diseases, infectious diseases, autoimmune diseases, and the like (Novina and Sharp, Nature, 430, 161-164, 2004). However, nucleic acids such as siRNA are difficult to deliver directly into cells and they are easily decomposed by enzymes in the blood, so there are many studies to overcome them. To date, the method for delivering nucleic acids into cells, a method for carrying by mixing with a positive charge lipid or polymer (named lipid-DNA conjugate (lipoplex) and polymer-DNA conjugate (polyplex), respectively) is mainly used (Hirko et al., Curr. Med. Chem., 10, 1185-93, 2003; Merdan et al., Adv. Drug. Deliv. Rev., 54, 715-58, 2002). The lipid-DNA conjugate is combined with the nucleic acid to deliver the nucleic acid well to cells and thus it is used a lot at the cell level, but in vivo, when injecting locally, in many cases, it has a disadvantage of inducing inflammation in the body (Filonand and Phillips, Biochim Biophys. Acta, 1329, 345-56, 1997).

In addition, such a non-viral delivery system has a problem of low transfection efficiency. Many efforts have been tilted to enhance transfection efficiency, but this is still far from the system that is stable. In addition, the carrier of the non-viral gene delivery system represents a significantly high cytotoxicity due to poor biocompatibility and non-biodegradability.

Under such a technical background, as the result that the present inventors have tried to develop a novel particle which has excellent encapsulation efficiency and can effectively deliver an anionic drug, a nucleic acid, and the like to a targeted organ or cell, they have completed the present invention by producing a lipid nanoparticle comprising an ionizable lipid; phospholipid; cholesterol; and a lipid-PEG (polyethyleneglycol) conjugate, and confirming that the lipid nanoparticle is delivered specifically to liver tissue and the drug such as anionic compound or nucleic acid can be encapsulated with high efficiency.

DISCLOSURE

Technical Problem

An object of the present invention is to provide a lipid nanoparticle comprising an ionizable lipid in which a 6-membered heterocyclic amine and an alkyl-epoxide are boned, a phospholipid, cholesterol and a lipid-PEG (polyethyleneglycol) conjugate.

Another object of the present invention is to provide a composition for delivering a drug (anionic drug, nucleic acid or a combination thereof) comprising (1) the lipid nanoparticle; and (2) an anionic drug, a nucleic acid, or a combination thereof.

Other object of the present invention is to provide a pharmaceutical composition for preventing or treating liver disease comprising (1) the lipid nanoparticle; and (2) an anionic drug, a nucleic acid, or a combination thereof.

Technical Solution

This will be described in detail as follows. On the other hand, each description and embodiment disclosed in the present invention may be applied to each other description and embodiment. In other words, all combinations of various elements disclosed herein fall within the scope of the present invention. In addition, it cannot be considered that the scope of the present invention is limited by the specific description described below.

One aspect to achieve the above object provides a lipid nanoparticle comprising an ionizable lipid in which a 6-membered heterocyclic amine and alkyl-epoxide are combined; phospholipid; cholesterol; and a lipid-PEG (polyethyleneglycol) conjugate.

The lipid nanoparticle according to one example is liver tissue-specific and has excellent biocompatibility and can deliver a gene therapeutic agent and the like with high efficiency, and thus it can be usefully used in related technical fields such as lipid nanoparticle-mediated gene therapy and image diagnosis technology.

Herein, 'ionizable lipid' or 'lipidoid' mean an amine-containing lipid which can be easily protonated, and for example, it may be a lipid of which charge state changes depending on the surrounding pH. The ionizable lipid may be one in which a 6-membered heterocyclic amine and alkyl-epoxide are combined. Specifically, the ionizable lipid may be a compound having characteristics similar to the lipid produced by reaction of the 6-membered heterocyclic amine and alkyl-epoxide, and more specifically, it may be a compound produced by ring opening reaction of epoxide by reacting the 6-membered heterocyclic amine with alkyl-epoxide.

In one example, the ionizable lipid may be one in which a 6-membered heterocyclic amine and alkyl-epoxide are combined by reacting them at a molar ratio of 1:n (n=number of primary amines comprised in 6-membered heterocyclic amine×2+number of secondary amines×1). According to one specific example, it may be prepared by mixing 246 amine and 1,2-epoxydodecane at a molar ratio of 1:4 and reacting them under the conditions of 700 to 800 rpm and 85 to 95 for 2 to 4 days.

The ionizable lipid may be protonated (positively charged) at a pH below the pKa of a cationic lipid, and it may be substantially neutral at a pH over the pKa. In one example, the lipid nanoparticle may comprise a protonated ionizable lipid and/or an ionizable lipid showing neutrality.

The ionizable lipid is an ionizable compound having characteristics similar to the lipid, and through electrostatic interaction with a drug (for example, anionic drug and/or nucleic acid), may play a role of encapsulating the drug within the lipid nanoparticle with high efficiency.

The 6-membered heterocyclic amine may comprise a structure of piperazine or piperidine.

The 6-membered heterocyclic amine may be a chain or non-chain amine comprising a tertiary amine, and according to one example, it may be one or more kinds selected from the group consisting of

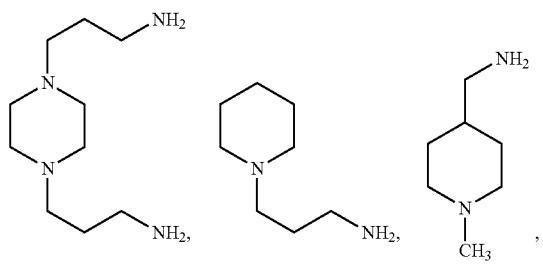

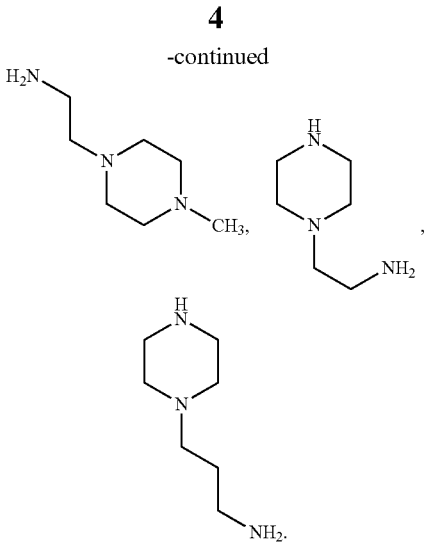

In one example, the 6-membered heterocyclic amine may be one or more kinds selected from the group consisting of 1,4-bis(3-aminopropyl)piperazine, N-(3-Aminopropyl)piperidine, (1-Methyl-4-piperidinyl)methanamine, 2-(4-Methyl-piperazin-1-yl)-ethylamine, 1-(2-Aminoethyl)piperazine, and 1-(3-aminopropyl)piperazine.

According to the type of the amine comprised in the ionizable lipid, (i) the drug encapsulation efficiency, (ii) PDI (polydispersity index), and/or (iii) the drug delivery efficiency to liver tissue and/or cells constituting liver (for example, hepatocyte) and/or LSEC (liver sinusoidal endothelial cell) of the lipid nanoparticle may be different.

The lipid nanoparticle comprising an ionizable lipid comprising an amine may have one or more kinds of the following characteristics:
(1) encapsulating a drug with high efficiency;
(2) uniform size of prepared particles (or having a low PDI value); and/or
(3) excellent drug delivery efficiency to liver tissue, and/or cells constituting liver (for example, hepatocyte and/or LSEC).

According to one example, a lipid nanoparticle comprising an ionizable lipid comprising 1,4-bis(3-aminopropyl) piperazine (for example, Cas Nos. 7209-38-3) may have one or more kinds of the following characteristics than a lipid nanoparticle comprising an ionizable lipid comprising other types of amines:
(1) encapsulating a drug with high efficiency;
(2) uniform size of prepared particles (or having a low PDI value); and/or
(3) excellent drug delivery efficiency to liver tissue, and/or cells constituting liver (for example, hepatocyte and/or LSEC).

The alkyl-epoxide may have the structure of Chemical formula 1 below.

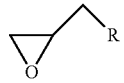

[Chemical formula 1]

The alkyl-epoxide may have a carbon length of C6 to C14, C6 to C12, C6 to C10, C8 to C14, C8 to C12, C8 to C10, C10 to C14, C10 to C12, or C10, and for example, it may be 1,2-epoxydodecane of C10. By setting the carbon number of the alkyl-epoxide comprised in the ionizable lipid to the above range, it is possible to represent a high encapsulation efficiency for the drug encapsulated in the lipid nanoparticle.

In one example, the ionizable lipid may have the general formula of Chemical formula 2 below.

[Chemical formula 2]

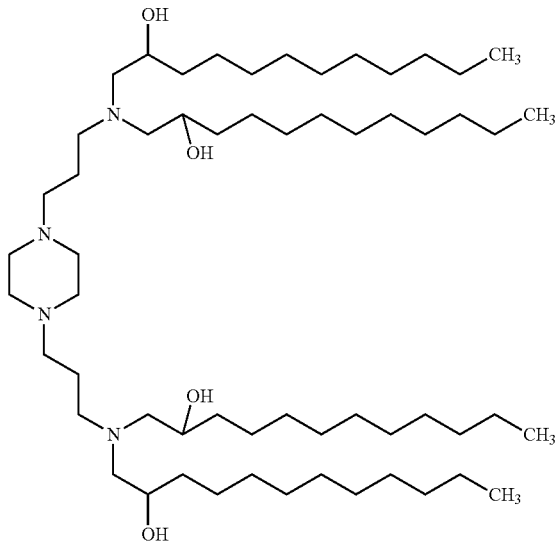 [SMILES: CCCCCCCCCCC(O)CN(CCCN1CCN(CCCN(CC(O)CCCCCCCCCC)CC(O)CCCCCCCCCC)CC1)CC(O)CCCCCCCCCC]

The structure of Chemical formula 2 is one example of the structure of the ionizable lipid according to one example, and the structure of the ionizable lipid may be different depending on the type of the 6-membered heterocyclic amine and alkyl-epoxide.

According to one example, a lipid nanoparticle comprising an ionizable lipid having the structure of Chemical formula 2 may have one or more kinds of the following characteristics than a lipid nanoparticle comprising other types of ionizable lipids:

(1) encapsulating a drug with high efficiency;
(2) uniform size of prepared particles (or having a low PDI value); and/or
(3) excellent drug delivery efficiency to liver tissue, and/or cells constituting liver (for example, hepatocyte and/or LSEC).

According to one example, the lipid nanoparticle may have a pKa of 5 to 8, 5.5 to 7.5, 6 to 7, or 6.5 to 7. The pKa is an acid dissociation constant, and refers to what is generally used as an index indicating the acid strength of a target substance. The pKa value of the lipid nanoparticle is important in terms of in vivo stability of the lipid nanoparticle and drug release of the lipid nanoparticle. In one example, the lipid nanoparticle showing the pKa value in the above range may be safely delivered to a target organ (for example, liver) and/or target cell (hepatocyte, and/or LSEC) in vivo, and reach to the target organ and/or target cell, and after endocytosis, exhibit a positive charge to release an encapsulated drug through electrostatic interaction with an anionic protein of the endosome membrane.

The phospholipid of the elements of the lipid nanoparticle according to one example plays a role of covering and protecting a core formed by interaction of the ionizable lipid and drug in the lipid nanoparticle, and may facilitate cell membrane permeation and endosomal escape during intracellular delivery of the drug by binding to the phospholipid bilayer of a target cell.

For the phospholipid, a phospholipid which can promote fusion of the lipid nanoparticle according to one example may be used without limitation, and for example, it may be one or more kinds selected from the group consisting of dioleoylphosphatidylethanolamine (DOPE), distearoylphosphatidylcholine (DSPC), palmitoyloleoylphosphatidylcholine (POPC), egg phosphatidylcholine (EPC), dioleoylphosphatidylcholine (DOPC), dipalmitoylphosphatidylcholine (DPPC), dioleoylphosphatidylglycerol (DOPG), dipalmitoylphosphatidylglycerol (DPPG), distearoylphosphatidylethanolamine (DSPE), phosphatidylethanolamine (PE), dipalmitoylphosphatidylethanolamine, 1,2-dioleoyl-sn-glycero-3-phosphoethanolamine, 1-palmitoyl-2-oleoyl-sn-glycero-3-phosphoethanolamine(POPE), 1-palmitoyl-2-oleoyl-sn-glycero-3-phosphocholine(POPC), 1,2-dioleoyl-sn-glycero-3-[phospho-L-serine](DOPS), 1,2-dioleoyl-sn-glycero-3-[phospho-L-serine] and the like. In one example, the lipid nanoparticle comprising DOPE may be effective in mRNA delivery (excellent drug delivery efficiency to mRNA), and in other example, the lipid nanoparticle comprising DSPE may be effective in siRNA delivery (excellent drug delivery efficiency to siRNA).

The cholesterol of the elements of the lipid nanoparticle according to one example may provide morphological rigidity to lipid filling in the lipid nanoparticle and be dispersed in the core and surface of the nanoparticle to improve the stability of the nanoparticle.

Herein, "lipid-PEG (polyethyleneglycol) conjugate", "lipid-PEG", "PEG-lipid", "PEG-lipid", or "lipid-PEG" refers to a form in which lipid and PEG are conjugated, and means a lipid in which a polyethylene glycol (PEG) polymer which is a hydrophilic polymer is bound to one end. The lipid-PEG conjugate contributes to the particle stability in serum of the nanoparticle within the lipid nanoparticle, and plays a role of preventing aggregation between nanoparticles. In addition, the lipid-PEG conjugate may protect nucleic acids from degrading enzyme during in vivo delivery of the nucleic acids and enhance the stability of nucleic acids in vivo and increase the half-life of the drug encapsulated in the nanoparticle.

In the lipid-PEG conjugate, the PEG may be directly conjugated to the lipid or linked to the lipid via a linker moiety. Any linker moiety suitable for binding PEG to the lipid may be used, and for example, includes an ester-free linker moiety and an ester-containing linker moiety. The ester-free linker moiety includes not only amido (—C(O)NH—), amino (—NR—), carbonyl (—C(O)—), carbamate (—NHC(O)O—), urea (—NHC(O)NH—), disulfide (—S—S—), ether (—O—), succinyl (—(O)CCH2CH2C(O)—), succinamidyl (—NHC(O)CH2CH2C(O)NH—), ether, disulfide but also combinations thereof (for example, a linker containing both a carbamate linker moiety and an amido linker moiety), but not limited thereto. The ester-containing linker moiety includes for example, carbonate (—OC(O)O—), succinoyl, phosphate ester (—O—(O)POH—O—), sulfonate ester, and combinations thereof, but not limited thereto.

In one example, the average molecular weight of the lipid-PEG conjugate may be 100 daltons to 10,000 daltons, 200 daltons to 8,000 daltons, 500 daltons to 5,000 daltons, 1,000 daltons to 3,000 daltons, 1,000 daltons to 2,600 daltons, 1,500 daltons to 2,600 daltons, 1,500 daltons to 2,500 daltons, 2,000 daltons to 2,600 daltons, 2,000 daltons to 2,500 daltons, or 2,000 daltons.

For the lipid in the lipid-PEG conjugate, any lipid capable of binding to polyethyleneglycol may be used without limitation, and the phospholipid and/or cholesterol which are other elements of the lipid nanoparticle may be also used. Specifically, the lipid in the lipid-PEG conjugate may be ceramide, dimyristoylglycerol (DMG), succinoyl-diacylglycerol (s-DAG), distearoylphosphatidylcholine (DSPC), distearoylphosphatidylethanolamine (DSPE), or cholesterol, but not limited thereto.

In one example, the lipid-PEG conjugate may be PEG bound to dialkyloxypropyl (PEG-DAA), PEG bound to diacylglycerol (PEG-DAG), PEG bound to phospholipid such as phosphatidylethanolamine (PEG-PE), PEG conjugated to ceramide (PEG-CER, ceramide-PEG conjugate, ceramide-PEG, PEG-ceramide conjugate or PEG-ceramide), cholesterol or PEG conjugated to derivative thereof, PEG-c-DOMG, PEG-DMG, PEG-DLPE, PEG-DMPE, PEG-DPPC, PEG-DSPE(DSPE-PEG), and a mixture thereof, and for example, may be C16-PEG2000 ceramide (N-palmitoyl-sphingosine-1-{succinyl[methoxy(polyethylene glycol)2000]}), DMG-PEG 2000, 14:0 PEG2000 PE.

According to one example, the case of comprising a lipid nanoparticle comprising a ceramide-PEG conjugate may have one or more kinds of the following characteristics than the case of comprising a lipid nanoparticle comprising other types of lipid-PEG conjugates:

(1) encapsulating a drug with high efficiency;
(2) uniform size of prepared particles (or having a low PDI value); and/or
(3) excellent drug delivery efficiency to liver tissue, and/or cells constituting liver (for example, hepatocyte and/or LSEC).

The PEG in the lipid-PEG conjugate is a hydrophilic polymer and has an ability to inhibit adsorption of serum proteins, and increases the circulation time of lipid nanoparticles in the body and can play a role of preventing aggregation between nanoparticles. In addition, the lipid-PEG conjugate may exhibit a stealth function in vivo to prevent degradation of nanoparticles.

The PEG may be what a functional group binds to a side not bound to a lipid (functionalized PEG). In this case, the functional group that can be used may be one or more kinds selected from the group consisting of succinyl group, carboxylic acid, maleimide, amine group, biotin, cyanur group and folate, and the like.

According to one example, the lipid-PEG conjugate may be comprised in the lipid nanoparticle in an amount of 0.1 to 15 mol %, 0.25 to 15 mol %, 0.5 to 15 mol %, 1 to 15 mol %, 1.5 to 15 mol %, 2 to 15 mol %, 2.5 to 15 mol %, 0.1 to 12.5 mol %, 0.25 to 12.5 mol %, 0.5 to 12.5 mol %, 1 to 12.5 mol %, 1.5 to 12.5 mol %, 2 to 12.5 mol %, 2.5 to 12.5 mol %, 0.1 to 10 mol %, 0.25 to 10 mol %, 0.5 to 10 mol %, 1 to 10 mol %, 1.5 to 10 mol %, 2 to 10 mol %, 2.5 to 10 mol %, 0.1 to 7.5 mol %, 0.25 to 7.5 mol %, 0.5 to 7.5 mol %, 1 to 7.5 mol %, 1.5 to 7.5 mol %, 2 to 7.5 mol %, 2.5 to 7.5 mol %, 0.1 to 5 mol %, 0.25 to 5 mol %, 0.5 to 5 mol %, 1 to 5 mol %, 1.5 to 5 mol %, 2 to 5 mol %, 2.5 to 5 mol %, 0.1 to 3 mol %, 0.25 to 3 mol %, 0.5 to 3 mol %, 1 to 3 mol %, 1.5 to 3 mol %, 2 to 3 mol %, 2.5 to 3 mol %, 0.1 to 2.5 mol %, 0.25 to 2.5 mol %, 0.5 to 2.5 mol %, 1 to 2.5 mol %, 1.5 to 2.5 mol %, 2 to 2.5 mol %, 0.1 to 4.5 mol %, 0.25 to 4.5 mol %, 0.5 to 4.5 mol %, 1 to 4.5 mol %, 1.5 to 4.5 mol %, 2 to 4.5 mol %, 2.5 to 4.5 mol %, 0.1 to 4 mol %, 0.25 to 4 mol %, 0.5 to 4 mol %, 1 to 4 mol %, 1.5 to 4 mol %, 2 to 4 mol %, 2.5 to 4 mol %, 0.1 to 3.5 mol %, 0.25 to 3.5 mol %, 0.5 to 3.5 mol %, 1 to 3.5 mol %, 1.5 to 3.5 mol %, 2 to 3.5 mol %, 2.5 to 3.5 mol %, 0.1 to 2.0 mol %, 0.1 to 1.5 mol %, 0.1 to 1.0 mol %, 0.5 to 2.0 mol %, 0.5 to 1.5 mol %, 0.5 to 1.0 mol %, 1.0 to 2.0 mol %, 1.0 to 1.5 mol %, 1.5 to 2.0 mol %, 1.0 mol %, or 1.5 mol %.

In one example, the liver tissue, hepatocytes and/or LSEC targeting effect (drug delivery effect) of the lipid nanoparticle may be dependent on the content of the lipid-PEG conjugate comprised in the lipid nanoparticle.

For example, the lipid nanoparticle comprising the lipid-PEG conjugate in an amount of 0.1 to 15 mol %, 0.25 to 15 mol %, 0.5 to 15 mol %, 1 to 15 mol %, 1.5 to 15 mol %, 2 to 15 mol %, 2.5 to 15 mol %, 0.1 to 12.5 mol %, 0.25 to 12.5 mol %, 0.5 to 12.5 mol %, 1 to 12.5 mol %, 1.5 to 12.5 mol %, 2 to 12.5 mol %, 2.5 to 12.5 mol %, 0.1 to 10 mol %, 0.25 to 10 mol %, 0.5 to 10 mol %, 1 to 10 mol %, 1.5 to 10 mol %, 2 to 10 mol %, 2.5 to 10 mol %, 0.1 to 7.5 mol %, 0.25 to 7.5 mol %, 0.5 to 7.5 mol %, 1 to 7.5 mol %, 1.5 to 7.5 mol %, 2 to 7.5 mol %, 2.5 to 7.5 mol %, 0.1 to 5 mol %, 0.25 to 5 mol %, 0.5 to 5 mol %, 1 to 5 mol %, 1.5 to 5 mol %, 2 to 5 mol %, 2.5 to 5 mol %, 0.1 to 3 mol %, 0.25 to 3 mol %, 0.5 to 3 mol %, 1 to 3 mol %, 1.5 to 3 mol %, 2 to 3 mol %, 2.5 to 3 mol %, 0.1 to 2.5 mol %, 0.25 to 2.5 mol %, 0.5 to 2.5 mol %, 1 to 2.5 mol %, 1.5 to 2.5 mol %, 2 to 2.5 mol %, 0.1 to 4.5 mol %, 0.25 to 4.5 mol %, 0.5 to 4.5 mol %, 1 to 4.5 mol %, 1.5 to 4.5 mol %, 2 to 4.5 mol %, 2.5 to 4.5 mol %, 0.1 to 4 mol %, 0.25 to 4 mol %, 0.5 to 4 mol %, 1 to 4 mol %, 1.5 to 4 mol %, 2 to 4 mol %, 2.5 to 4 mol %, 0.1 to 3.5 mol %, 0.25 to 3.5 mol %, 0.5 to 3.5 mol %, 1 to 3.5 mol %, 1.5 to 3.5 mol %, 2 to 3.5 mol %, 2.5 to 3.5 mol %, 0.1 to 10 mol %, 0.1 to 5.0 mol %, 0.1 to 4.5 mol %, 0.1 to 4.0 mol %, 0.1 to 3.5 mol %, 0.1 to 3.0 mol %, 0.1 to 2.5 mol %, 0.1 to 2.0 mol %, 0.1 to 1.5 mol %, 0.1 to 1.0 mol %, 0.5 to 10 mol %, 0.5 to 5.0 mol %, 0.5 to 4.5 mol %, 0.5 to 4.0 mol %, 0.5 to 3.5 mol %, 0.5 to 3.0 mol %, 0.5 to 2.5 mol %, 0.5 to 2.0 mol %, 0.5 to 1.5 mol %, 0.5 to 1.0 mol %, 1.0 to 10 mol %, 1.0 to 5.0 mol %, 1.0 to 4.5 mol %, 1.0 to 4.0 mol %, 1.0 to 3.5 mol %, 1.0 to 3.0 mol %, 1.0 to 2.5 mol %, 1.0 to 2.0 mol %, 1.0 to 1.5 mol %, 1.5 to 10 mol %, 1.5 to 5.0 mol %, 1.5 to 4.5 mol %, 1.5 to 4.0 mol %, 1.5 to 3.5 mol %, 1.5 to 3.0 mol %, 1.5 to 2.5 mol %, 1.5 to 2.0 mol %, 1.0 mol %, or 1.5 mol % (than the lipid nanoparticle comprising the lipid-PEG conjugate in a content outside the above range) may have an excellent targeting effect to hepatocytes.

As another example, the lipid nanoparticle comprising the lipid-PEG conjugate in an amount of 0.1 to 15 mol %, 0.25 to 15 mol %, 0.5 to 15 mol %, 1 to 15 mol %, 1.5 to 15 mol %, 2 to 15 mol %, 2.5 to 15 mol %, 0.1 to 12.5 mol %, 0.25 to 12.5 mol %, 0.5 to 12.5 mol %, 1 to 12.5 mol %, 1.5 to 12.5 mol %, 2 to 12.5 mol %, 2.5 to 12.5 mol %, 0.1 to 10 mol %, 0.25 to 10 mol %, 0.5 to 10 mol %, 1 to 10 mol %, 1.5 to 10 mol %, 2 to 10 mol %, 2.5 to 10 mol %, 0.1 to 7.5 mol %, 0.25 to 7.5 mol %, 0.5 to 7.5 mol %, 1 to 7.5 mol %, 1.5 to 7.5 mol %, 2 to 7.5 mol %, 2.5 to 7.5 mol %, 0.1 to 5 mol %, 0.25 to 5 mol %, 0.5 to 5 mol %, 1 to 5 mol %, 1.5 to 5 mol %, 2 to 5 mol %, 2.5 to 5 mol %, 0.1 to 3 mol %, 0.25 to 3 mol %, 0.5 to 3 mol %, 1 to 3 mol %, 1.5 to 3 mol %, 2 to 3 mol %, 2.5 to 3 mol %, 0.1 to 2.5 mol %, 0.25 to 2.5 mol %, 0.5 to 2.5 mol %, 1 to 2.5 mol %, 1.5 to 2.5 mol %, 2 to 2.5 mol %, 0.1 to 4.5 mol %, 0.25 to 4.5 mol %, 0.5 to 4.5 mol %, 1 to 4.5 mol %, 1.5 to 4.5 mol %, 2 to 4.5 mol %, 2.5 to 4.5 mol %, 0.1 to 4 mol %, 0.25 to 4 mol %, 0.5 to 4 mol %, 1 to 4 mol %, 1.5 to 4 mol %, 2 to 4 mol %, 2.5 to 4 mol %, 0.1 to 3.5 mol %, 0.25 to 3.5 mol %, 0.5 to 3.5 mol %, 1 to 3.5 mol %, 1.5 to 3.5 mol %, 2 to 3.5 mol %, 2.5 to 3.5 mol %, 0.1 to 10 mol %, 0.1 to 5.0 mol %, 0.1 to 4.5 mol %, 0.1 to 4.0 mol %, 0.1 to 3.5 mol %, 0.1 to 3.0 mol %, 0.1 to 2.5 mol %, 0.1 to 2.0 mol %, 0.1 to 1.5 mol %, 0.1 to 1.0 mol %, 0.5 to 10 mol %, 0.5 to 5.0 mol %, 0.5 to 4.5 mol %, 0.5 to 4.0 mol %, 0.5 to 3.5 mol %, 0.5 to 3.0 mol %, 0.5 to 2.5 mol %, 0.5 to 2.0 mol %, 0.5 to 1.5 mol %, 0.5 to 1.0 mol %, 1.0 to 10 mol %, 1.0 to 5.0 mol %, 1.0 to 4.5 mol %, 1.0 to 4.0 mol %, 1.0 to 3.5 mol %, 1.0 to 3.0 mol %, 1.0 to 2.5 mol %, 1.0 to 2.0 mol %, 1.0 to 1.5 mol %, 1.5 to 10 mol %, 1.5 to 5.0 mol %, 1.5 to 4.5 mol %, 1.5 to 4.0 mol %, 1.5 to 3.5 mol %, 1.5 to 3.0 mol %, 1.5 to 2.5 mol %, 1.5 to 2.0 mol %, 1.0 mol %, or 1.5 mol % (than the lipid nanoparticle comprising the lipid-PEG conjugate in a content outside the above range) may have an excellent targeting effect to LSEC.

According to one example, the cholesterol may be comprised in the lipid nanoparticle in an amount of 10 to 60 mol %, 20 to 60 mol %, 30 to 60 mol %, 30 to 55 mol %, 30 to 52.5 mol %, 30 to 52 mol %, 30 to 51 mol %, 30 to 50 mol %, 30 to 47.5 mol %, 30 to 45 mol %, 30 to 44 mol %, 30 to 43.5 mol %, 30 to 43 mol %, 30 to 41.5 mol %, 30 to 40 mol %, 30 to 39.5 mol %, 35 to 60 mol %, 35 to 55 mol %, 35 to 52.5 mol %, 35 to 52 mol %, 35 to 51 mol %, 35 to 50 mol %, 35 to 47.5 mol %, 35 to 45 mol %, 35 to 44 mol %, 35 to 43.5 mol %, 35 to 43 mol %, 35 to 41.5 mol %, 35 to 40 mol %, 35 to 39.5 mol %, 37 to 60 mol %, 37 to 55 mol %, 37 to 52.5 mol %, 37 to 52 mol %, 37 to 51 mol %, 37.5 to 50 mol %, 37.5 to 47.5 mol %, 37.5 to 45 mol %, 37.5 to 44 mol %, 37.5 to 43.5 mol %, 37.5 to 43 mol %, 37.5 to 41.5 mol %, 37.5 to 40 mol %, 37.5 to 39.5 mol %, 39.5 to 60 mol %, 39.5 to 55 mol %, 39.5 to 52.5 mol %, 39.5 to 52 mol %, 39.5 to 51 mol %, 39.5 to 50 mol %, 39.5 to 47.5 mol %, 39.5 to 45 mol %, 39.5 to 44 mol %, 39.5 to 43.5 mol %, 39.5 to 43 mol %, 39.5 to 41.5 mol %, 39.5 to 40 mol %, 40 to 60 mol %, 40 to 55 mol %, 40 to 52.5 mol %, 40 to 52 mol %, 40 to 51 mol %, 40 to 50 mol %, 40 to 47.5 mol %, 40 to 45 mol %, 40 to 44 mol %, 40 to 43.5 mol %, 40 to 43 mol %, 40 to 41.5 mol %, 41.5 to 60 mol %, 41.5 to 55 mol %, 41.5 to 52.5 mol %, 41.5 to 52 mol %, 41.5 to 51 mol %, 41.5 to 50 mol %, 41.5 to 47.5 mol %, 41.5 to 45 mol %, 41.5 to 44 mol %, 41.5 to 43.5 mol %, 41.5 to 43 mol %, 43 to 60 mol %, 43 to 55 mol %, 43 to 52.5 mol %, 43 to 52 mol %, 43 to 51 mol %, 43 to 50 mol %, 43 to 47.5 mol %, 43 to 45 mol %, 43 to 44 mol %, 43 to 43.5 mol %, 43.5 to 60 mol %, 43.5 to 55 mol %, 43.5 to 52.5 mol %, 43.5 to 52 mol %, 43.5 to 51 mol %, 43.5 to 50 mol %, 43.5 to 47.5 mol %, 43.5 to 45 mol %, 43.5 to 44 mol %, 45 to 60 mol %, 45 to 55 mol %, 45 to 52.5 mol %, 45 to 52 mol %, 45 to 51 mol %, 45 to 50 mol %, 45 to 47.5 mol %, 47.5 to 60 mol %, 47.5 to 55 mol %, 47.5 to 52.5 mol %, 47.5 to 52 mol %, 47.5 to 51 mol %, 47.5 to 50 mol %,%, 50 to 60 mol %, 50 to 55 mol %, 50 to 52.5 mol %, 50 to 52 mol %, 50 to 52.5 mol % 50 to 51.5 mol %, 51 to 60 mol %, 51 to 55 mol %, 51 to 52.5 mol %, or 51 to 52 mol %, %, 51 to 60 mol %, 51 to 55 mol %, 51 to 52.5 mol %, or 51 to 52 mol %.

According to one example, the sum of the lipid-PEG conjugate and cholesterol may be comprised in the lipid nanoparticle in an amount of 30 to 70 mol %, 40 to 70 mol %, 40 to 60 mol %, 40 to 55 mol %, 40 to 53.5 mol %, 40 to 50 mol %, 40 to 47.5 mol %, 40 to 45 mol %, 40 to 44.5 mol %, 42 to 60 mol %, 42 to 55 mol %, 42 to 53.5 mol %, 42 to 50 mol %, 42 to 47.5 mol %, 42 to 45 mol %, 42 to 44.5 mol %, 44 to 60 mol %, 44 to 55 mol %, 44 to 53.5 mol %, 44 to 50 mol %, 44 to 47.5 mol %, 44 to 45 mol %, 44 to 44.5 mol %, 44.5 to 60 mol %, 44.5 to 55 mol %, 44.5 to 53.5 mol %, 44.5 to 50 mol %, 44.5 to 47.5 mol %, or 44.5 to 45 mol %.

According to one example, the ionizable lipid may be comprised in the lipid nanoparticle in an amount of 10 to 70 mol %, 10 to 60 mol %, 10 to 55 mol %, 10 to 50 mol %, 10 to 45 mol %, 10 to 42.5 mol %, 10 to 40 mol %, 10 to 35 mol %, 10 to 30 mol %, 10 to 26.5 mol %, 10 to 25 mol %, 10 to 20 mol %, 15 to 60 mol %, 15 to 55 mol %, 15 to 50 mol %, 15 to 45 mol %, 15 to 42.5 mol %, 15 to 40 mol %, 15 to 35 mol %, 15 to 30 mol %, 15 to 26.5 mol %, 15 to 25 mol %, 15 to 20 mol %, 20 to 60 mol %, 20 to 55 mol %, 20 to 50 mol %, 20 to 45 mol %, 20 to 42.5 mol %, 20 to 40 mol %, 20 to 35 mol %, 20 to 30 mol %, 20 to 26.5 mol %, 20 to 25 mol %, 25 to 60 mol %, 25 to 55 mol %, 25 to 50 mol %, 25 to 45 mol %, 25 to 42.5 mol %, 25 to 40 mol %, 25 to 35 mol %, 25 to 30 mol %, 25 to 26.5 mol %, 26.5 to 60 mol %, 26.5 to 55 mol %, 26.5 to 50 mol %, 26.5 to 45 mol %, 26.5 to 42.5 mol %, 26.5 to 40 mol %, 26.5 to 35 mol %, 26.5 to 30 mol %, 30 to 60 mol %, 30 to 55 mol %, 30 to 50 mol %, 30 to 45 mol %, 30 to 42.5 mol %, 30 to 40 mol %, 30 to 35 mol %, 35 to 60 mol %, 35 to 55 mol %, 35 to 50 mol %, 35 to 45 mol %, 35 to 42.5 mol %, 35 to 40 mol %, 40 to 60 mol %, 40 to 55 mol %, 40 to 50 mol %, 40 to 45 mol %, 40 to 42.5 mol %, 42.5 to 60 mol %, 42.5 to 55 mol %, 42.5 to 50 mol %, or 42.5 to 45 mol %.

According to one example, the phospholipid may be comprised in the lipid nanoparticle in an amount of 1 to 50 mol %, 5 to 50 mol %, 5 to 40 mol %, 5 to 30 mol %, 5 to 25 mol %, 5 to 20 mol %, 5 to 15 mol %, 5 to 13 mol %, 5 to 10 mol %, 10 to 30 mol %, 10 to 25 mol %, 10 to 20 mol %, 10 to 15 mol %, 10 to 13 mol %, 15 to 30 mol %, 15 to 25 mol %, 15 to 20 mol %, 20 to 30 mol %, or 20 to 25 mol %.

Herein, "mol % (mol %, mole percentage)" is expressed as a percentage by dividing the number of moles of a specific component by the sum of moles of all components and then multiplying by 100, and expressed as a formula, for example, it may be as Equation 1 below.

mol %=(moles of a specific component)/(sum of moles of all components)×100 (Equation 1)

The lipid nanoparticle may comprise the ionizable lipid: phospholipid:cholesterol:lipid-PEG conjugate at a molar ratio of 20 to 50:10 to 30:20 to 60:0.1 to 10, at a molar ratio of 20 to 50:10 to 30:20 to 60:0.25 to 10, at a molar ratio of 20 to 50:10 to 30:30 to 60:0.25 to 10, at a molar ratio of 20 to 50:10 to 30:30 to 60:0.1 to 5, at a molar ratio of 20 to 50:10 to 30:30 to 60:0.5 to 5, at a molar ratio of 25 to 45:10 to 25:40 to 50:0.5 to 3, at a molar ratio of 25 to 45:10 to 20:40 to 55:0.5 to 3, at a molar ratio of 25 to 45:10 to 20:40 to 55:1.0 to 1.5, at a molar ratio of 40 to 45:10 to 15:40 to 45:0.5 to 3.0, at a molar ratio of 40 to 45:10 to 15:40 to 45:0.5 to 3, at a molar ratio of 40 to 45:10 to 15:40 to 45:1 to 1.5, at a molar ratio of 25 to 30:17 to 22; 50 to 55:0.5 to 3.0, at a molar ratio of 25 to 30:17 to 22; 50 to 55:1.0 to 2.5, or at a molar ratio of 25 to 30:17 to 22; 50 to 55:1.5 to 2.5. According to one example, while maintaining the sum of the moles of the lipid-PEG conjugate and cholesterol constant, among the components comprised in the lipid nanoparticle, the moles of cholesterol are decreased as much as the number of moles of the lipid-PEG conjugate is increased, and thereby the molar ratio of the components can be maintained.

Herein, the molar ratio means a ratio of moles, and "part of weight" mean a weight ratio in which each component is comprised.

In one example, the lipid nanoparticle may comprise the ionizable lipid of 20 to 50 parts by weight, phospholipid of 10 to 30 parts by weight, cholesterol of 20 to 60 parts by weight (or 20 to 60 parts by weight), and lipid-PEG conjugate of 0.1 to 10 parts by weight (or 0.25 to 10 parts by weight, 0.5 to 5 parts by weight). The lipid nanoparticle may comprise the ionizable lipid of 20 to 50% by weight, phospholipid of 10 to 30% by weight, cholesterol of 20 to 60% by weight (or 30 to 60% by weight), and lipid-PEG conjugate of 0.1 to 10% by weight (or 0.25 to 10% by weight, 0.5 to 5% by weight) based on the total nanoparticle weight. In other example, the lipid nanoparticle may comprise the ionizable lipid of 25 to 50% by weight, phospholipid of 10 to 20% by weight, cholesterol of 35 to 55% by weight, and lipid-PEG conjugate of 0.1 to 10% by weight (or 0.25 to 10% by weight, 0.5 to 5% by weight), based on the total nanoparticle weight.

The lipid nanoparticle comprising the ionizable lipid, cholesterol, phospholipid, and/or lipid-PEG conjugate in the above range (molar ratio, part by weight, and/or % by weight) may have excellent (i) stability of the lipid nanoparticle, (ii) encapsulation efficiency of the drug, and/or (iii) drug delivery efficiency targeting liver tissue and/or cells (for example, hepatocytes and/or LSEC), than the lipid nanoparticle comprising the ionizable lipid, cholesterol, phospholipid and/or lipid-PEG conjugate outside the above range.

The lipid nanoparticle according to one example may have an average diameter of 20 nm to 200 nm, 20 to 180 nm, 20 nm to 170 nm, 20 nm to 150 nm, 20 nm to 120 nm, 20 nm to 100 nm, 20 nm to 90 nm, 30 nm to 200 nm, 30 to 180 nm, 30 nm to 170 nm, 30 nm to 150 nm, 30 nm to 120 nm, 30 nm to 100 nm, 30 nm to 90 nm, 40 nm to 200 nm, 40 to 180 nm, 40 nm to 170 nm, 40 nm to 150 nm, 40 nm to 120 nm, 40 nm to 100 nm, 40 nm to 90 nm, 50 nm to 200 nm, 50 to 180 nm, 50 nm to 170 nm, 50 nm to 150 nm, 50 nm to 120 nm, 50 nm to 100 nm, 50 nm to 90 nm, 60 nm to 200 nm, 60 to 180 nm, 60 nm to 170 nm, 60 nm to 150 nm, 60 nm to 120 nm, 60 nm to 100 nm, 60 nm to 90 nm, 70 nm to 200 nm, 70 to 180 nm, 70 nm to 170 nm, 70 nm to 150 nm, 70 nm to 120 nm, 70 nm to 100 nm, 70 nm to 90 nm, 80 nm to 200 nm, 80 to 180 nm, 80 nm to 170 nm, 80 nm to 150 nm, 80 nm to 120 nm, 80 nm to 100 nm, 80 nm to 90 nm, 90 nm to 200 nm, 90 to 180 nm, 90 nm to 170 nm, 90 nm to 150 nm, 90 nm to 120 nm, or 90 nm to 100 nm, for easy introduction into liver tissue, hepatocytes and/or LSEC (liver sinusoidal endothelial cells). When the size of the lipid nanoparticle is smaller than the above range, it is difficult to maintain stability as the surface area of the lipid nanoparticle is excessively increased, and thus delivery to the target tissue and/or drug effect may be reduced.

The liver tissue, hepatocytes and/or LSEC targeting effect (drug delivery effect) of the lipid nanoparticle according to one example may be dependent on the size of the lipid nanoparticle. For example, in case of the lipid nanoparticle having a diameter of 40 to 120 nm, 30 to 100 nm, 35 to 95 nm, 40 to 90 nm, 45 to 90 nm, 50 to 90 nm, 55 to 85 nm, 60 to 80 nm, 70 to 90 nm, 70 to 80 nm, 50 to 70 nm, or 60 to 70 nm, the targeting effect to hepatocytes may be excellent (than the nanoparticle having a diameter outside the above range). As another example, in case of the lipid nanoparticle having a diameter of 20 to 200 nm, 20 to 180 nm, 40 to 180 nm, 40 to 170 nm, 50 to 160 nm, 70 to 180 nm, 70 to 170 nm, 75 to 170 nm, 75 to 165 nm, 70 to 150 nm, 70 to 130 nm, 75 to 130 nm, 80 to 120 nm, 85 to 120 nm, about 90 to 120 nm, 90 to 110 nm, 90 to 100 nm, 80 to 110 nm, 80 to 100 nm, 85 to 95 nm, about 90 nm, or 90 nm, the targeting effect to LSEC may be excellent (than the nanoparticle having a diameter outside the above range).

The lipid nanoparticle may specifically target liver tissue. The lipid nanoparticle according to one example may imitate metabolic behaviors of natural lipoproteins very similarly, and may be usefully applied for the lipid metabolism process by the liver and therapeutic mechanism through this.

The lipid nanoparticle may target hepatocytes. When the content of the lipid-PEG content comprised in the lipid nanoparticle is 0.1 to 15 mol %, 0.25 to 15 mol %, 0.5 to 15 mol %, 1 to 15 mol %, 1.5 to 15 mol %, 2 to 15 mol %, 2.5 to 15 mol %, 0.1 to 12.5 mol %, 0.25 to 12.5 mol %, 0.5 to 12.5 mol %, 1 to 12.5 mol %, 1.5 to 12.5 mol %, 2 to 12.5 mol %, 2.5 to 12.5 mol %, 0.1 to 10 mol %, 0.25 to 10 mol %, 0.5 to 10 mol %, 1 to 10 mol %, 1.5 to 10 mol %, 2 to 10 mol %, 2.5 to 10 mol %, 0.1 to 7.5 mol %, 0.25 to 7.5 mol %, 0.5 to 7.5 mol %, 1 to 7.5 mol %, 1.5 to 7.5 mol %, 2 to 7.5 mol %, 2.5 to 7.5 mol %, 0.1 to 5 mol %, 0.25 to 5 mol %, 0.5 to 5 mol %, 1 to 5 mol %, 1.5 to 5 mol %, 2 to 5 mol %, 2.5 to 5 mol %, 0.1 to 3 mol %, 0.25 to 3 mol %, 0.5 to 3 mol %, 1 to 3 mol %, 1.5 to 3 mol %, 2 to 3 mol %, 2.5 to 3 mol %, 0.1 to 2.5 mol %, 0.25 to 2.5 mol %, 0.5 to 2.5 mol %, 1 to 2.5 mol %, 1.5 to 2.5 mol %, 2 to 2.5 mol %, 0.1 to 4.5 mol %, 0.25 to 4.5 mol %, 0.5 to 4.5 mol %, 1 to 4.5 mol %, 1.5 to 4.5 mol %, 2 to 4.5 mol %, 2.5 to 4.5 mol %, 0.1 to 4 mol %, 0.25 to 4 mol %, 0.5 to 4 mol %, 1 to 4 mol %, 1.5 to 4 mol %, 2 to 4 mol %, 2.5 to 4 mol %, 0.1 to 3.5 mol %, 0.25 to 3.5 mol %, 0.5 to 3.5 mol %, 1 to 3.5 mol %, 1.5 to 3.5 mol %, 2 to 3.5 mol %, 2.5 to 3.5 mol %, 0.1 to 2.0 mol %, 0.1 to 1.5 mol %, 0.1 to 1.0 mol %, 0.5 to 2.0 mol %, 0.5 to 1.5 mol %, 0.5 to 1.0 mol %, 1.0 to 2.0 mol %, 1.0 to 1.5 mol %, 1.5 to 2.0 mol %, 1.0 mol %, or 1.5 mol %, the drug delivery efficiency (hepatocyte targeting efficiency) to hepatocytes of the lipid nanoparticle may be excellent.

The lipid nanoparticle may target an LSEC (liver sinusoidal endothelial cell). When the content of the lipid-PEG content comprised in the lipid nanoparticle is 0.1 to 15 mol %, 0.25 to 15 mol %, 0.5 to 15 mol %, 1 to 15 mol %, 1.5 to 15 mol %, 2 to 15 mol %, 2.5 to 15 mol %, 0.1 to 12.5 mol %, 0.25 to 12.5 mol %, 0.5 to 12.5 mol %, 1 to 12.5 mol %, 1.5 to 12.5 mol %, 2 to 12.5 mol %, 2.5 to 12.5 mol %, 0.1 to 10 mol %, 0.25 to 10 mol %, 0.5 to 10 mol %, 1 to 10 mol %, 1.5 to 10 mol %, 2 to 10 mol %, 2.5 to 10 mol %, 0.1 to 7.5 mol %, 0.25 to 7.5 mol %, 0.5 to 7.5 mol %, 1 to 7.5 mol %, 1.5 to 7.5 mol %, 2 to 7.5 mol %, 2.5 to 7.5 mol %, 0.1 to 5 mol %, 0.25 to 5 mol %, 0.5 to 5 mol %, 1 to 5 mol %, 1.5 to 5 mol %, 2 to 5 mol %, 2.5 to 5 mol %, 0.1 to 3 mol %, 0.25 to 3 mol %, 0.5 to 3 mol %, 1 to 3 mol %, 1.5 to 3 mol %, 2 to 3 mol %, 2.5 to 3 mol %, 0.1 to 2.5 mol %, 0.25 to 2.5 mol %, 0.5 to 2.5 mol %, 1 to 2.5 mol %, 1.5 to 2.5 mol %, 2 to 2.5 mol %, 0.1 to 4.5 mol %, 0.25 to 4.5 mol %, 0.5 to 4.5 mol %, 1 to 4.5 mol %, 1.5 to 4.5 mol %, 2 to 4.5 mol %, 2.5 to 4.5 mol %, 0.1 to 4 mol %, 0.25 to 4 mol %, 0.5 to 4 mol %, 1 to 4 mol %, 1.5 to 4 mol %, 2 to 4 mol %, 2.5 to 4 mol %, 0.1 to 3.5 mol %, 0.25 to 3.5 mol %, 0.5 to 3.5 mol %, 1 to 3.5 mol %, 1.5 to 3.5 mol %, 2 to 3.5 mol %, 2.5 to 3.5 mol %, 0.1 to 2.0 mol %, 0.1 to 1.5 mol %, 0.1 to 1.0 mol %, 0.5 to 2.0 mol %, 0.5 to 1.5 mol %, 0.5 to 1.0 mol %, 1.0 to 2.0 mol %, 1.0 to 1.5 mol %, 1.5 to 2.0 mol %, 1.0 mol %, or 1.5 mol %, the drug delivery efficiency (LSEC targeting efficiency) to LSEC of the lipid nanoparticle may be excellent.

Herein, "targeting" and "localization" to the liver tissue, hepatocytes and/or LSEC of the lipid nanoparticle may be internalization in the tissue or cells, and may mean internalization inside the nucleus as it can penetrate the nuclear membrane.

As other aspect, a composition for drug delivery comprising (i) the lipid nanoparticle; and (ii) an anionic drug, nucleic acid or combination thereof (combination of the anionic drug and nucleic acid) is provided. The drug may be an anionic drug, nucleic acid or combination thereof (anionic drug and nucleic acid).

The composition for drug delivery may be what a bioactive substance such as an anionic drug and/or nucleic acid, and the like may be encapsulated inside the lipid nanoparticle, and the bioactive substance such as an anionic drug and/or nucleic acid may be encapsulated with stable and high efficiency and thereby, it may show an excellent therapeutic effect by the composition for delivery. In addition, there is an advantage of variously controlling the kinds of the drug to be encapsulated in the lipid nanoparticle according to the purpose of treatment.

The lipid nanoparticle may have an anionic drug and/or nucleic acid encapsulated inside (the lipid nanoparticle). For the lipid nanoparticle in which an anionic drug and/or nucleic acid is encapsulated (inside the lipid nanoparticle) is the same as for the lipid nanoparticle described above.

In one example, the weight ratio of the ionizable lipid and drug (anionic drug, nucleic acid or combination thereof) comprised in the lipid nanoparticle may be 1 to 20:1, 1 to 15:1, 1 to 10:1, 5 to 20:1, 5 to 15:1, 5 to 10:1, 7.5 to 20:1, 7.5 to 15:1, or 7.5 to 10:1.

In one example, when the (i) ionizable lipid; and (2) drug (anionic drug, nucleic acid or combination thereof) are comprised at a weight ratio in the above range, the encapsulation efficiency of the drug (anionic drug, nucleic acid or combination thereof) inside the lipid nanoparticle and/or drug delivery efficiency may be higher than the lipid nanoparticle comprising the (1) ionizable lipid; and (2) anionic drug, nucleic acid or combination thereof at a weight ratio outside the above range.

The lipid nanoparticle in which the anionic drug and/or nucleic acid is encapsulated may have an average diameter of 20 nm to 200 nm, 20 to 180 nm, 20 nm to 170 nm, 20 nm to 150 nm, 20 nm to 120 nm, 20 nm to 100 nm, 20 nm to 90 nm, 30 nm to 200 nm, 30 to 180 nm, 30 nm to 170 nm, 30 nm to 150 nm, 30 nm to 120 nm, 30 nm to 100 nm, 30 nm to 90 nm, 40 nm to 200 nm, 40 to 180 nm, 40 nm to 170 nm, 40 nm to 150 nm, 40 nm to 120 nm, 40 nm to 100 nm, 40 nm to 90 nm, 50 nm to 200 nm, 50 to 180 nm, 50 nm to 170 nm, 50 nm to 150 nm, 50 nm to 120 nm, 50 nm to 100 nm, 50 nm to 90 nm, 60 nm to 200 nm, 60 to 180 nm, 60 nm to 170 nm, 60 nm to 150 nm, 60 nm to 120 nm, 60 nm to 100 nm, 60 nm to 90 nm, 70 nm to 200 nm, 70 to 180 nm, 70 nm to 170 nm, 70 nm to 150 nm, 70 nm to 120 nm, 70 nm to 100 nm, 70 nm to 90 nm, 80 nm to 200 nm, 80 to 180 nm, 80 nm to 170 nm, 80 nm to 150 nm, 80 nm to 120 nm, 80 nm to 100 nm, 80 nm to 90 nm, 90 nm to 200 nm, 90 to 180 nm, 90 nm to 170 nm, 90 nm to 150 nm, 90 nm to 120 nm, or 90 nm to 100 nm, so that the introduction into the liver tissue, hepatocytes and/or LSEC (liver sinusoidal endothelial cells) is easy.

When the size of the lipid nanoparticle is smaller than the lower limit of the above range, (i) during systemic circulation of the lipid nanoparticle, binding of apolipoproteins (for example, ApoE (e.g. ApoE3)) present in blood is reduced, and therefore, the number of the lipid nanoparticles entering the cells may be reduced and/or (ii) the surface area of the lipid nanoparticle is excessively increased and therefore it is difficult to maintain the stability, and thus the drug delivery efficiency to target tissue (or target cell) and/or therapeutic effect of the drug which the lipid nanoparticle carries out may be reduced.

The lipid nanoparticle having a diameter in the above range has excellent drug delivery efficiency to a target organ and/or cell than the lipid nanoparticle having a diameter over the upper limit of the above range.

In one example, the composition for drug delivery comprising (1) the lipid nanoparticle; and (2) anionic drug, nucleic acid or combination thereof may be a composition for drug delivery to hepatocytes.

According to one example, the diameter of the lipid nanoparticle comprised in the composition for drug (anionic drug, nucleic acid or combination thereof) delivery to hepatocytes may be 40 to 120 nm, 30 to 100 nm, 35 to 95 nm, 40 to 90 nm, 45 to 90 nm, 50 to 90 nm, 55 to 85 nm, 60 to 80 nm, 70 to 90 nm, 70 to 80 nm, 50 to 70 nm, or 60 to 70 nm. During the drug delivery to hepatocytes, the diameter of the fenestrae leading from the sinusoidal lumen to the hepatocytes is about 140 nm in mammals and about 100 nm in humans, so the composition for drug delivery having a diameter in the above range may have excellent drug delivery efficiency to hepatocytes than the lipid nanoparticle having the diameter outside the above range.

According to one example, the lipid nanoparticle comprised in the composition for drug delivery to hepatocytes may comprise the lipid-PEG conjugate in an amount of 0.1 to 15 mol %, 0.25 to 15 mol %, 0.5 to 15 mol %, 1 to 15 mol %, 1.5 to 15 mol %, 2 to 15 mol %, 2.5 to 15 mol %, 0.1 to 12.5 mol %, 0.25 to 12.5 mol %, 0.5 to 12.5 mol %, 1 to 12.5 mol %, 1.5 to 12.5 mol %, 2 to 12.5 mol %, 2.5 to 12.5 mol %, 0.1 to 10 mol %, 0.25 to 10 mol %, 0.5 to 10 mol %, 1 to 10 mol %, 1.5 to 10 mol %, 2 to 10 mol %, 2.5 to 10 mol %, 0.1 to 7.5 mol %, 0.25 to 7.5 mol %, 0.5 to 7.5 mol %, 1 to 7.5 mol %, 1.5 to 7.5 mol %, 2 to 7.5 mol %, 2.5 to 7.5 mol %, 0.1 to 5 mol %, 0.25 to 5 mol %, 0.5 to 5 mol %, 1 to 5 mol %, 1.5 to 5 mol %, 2 to 5 mol %, 2.5 to 5 mol %, 0.1 to 3 mol %, 0.25 to 3 mol %, 0.5 to 3 mol %, 1 to 3 mol %, 1.5 to 3 mol %, 2 to 3 mol %, 2.5 to 3 mol %, 0.1 to 2.5 mol %, 0.25 to 2.5 mol %, 0.5 to 2.5 mol %, 1 to 2.5 mol %, 1.5 to 2.5 mol %, 2 to 2.5 mol %, 0.1 to 4.5 mol %, 0.25 to 4.5 mol %, 0.5 to 4.5 mol %, 1 to 4.5 mol %, 1.5 to 4.5 mol %, 2 to 4.5 mol %, 2.5 to 4.5 mol %, 0.1 to 4 mol %, 0.25 to 4 mol %, 0.5 to 4 mol %, 1 to 4 mol %, 1.5 to 4 mol %, 2 to 4 mol %, 2.5 to 4 mol %, 0.1 to 3.5 mol %, 0.25 to 3.5 mol %, 0.5 to 3.5 mol %, 1 to 3.5 mol %, 1.5 to 3.5 mol %, 2 to 3.5 mol %, 2.5 to 3.5 mol %, 0.1 to 2.0 mol %, 0.1 to 1.5 mol %, 0.1 to 1.0 mol %, 0.5 to 2.0 mol %, 0.5 to 1.5 mol %, 0.5 to 1.0 mol %, 1.0 to 2.0 mol %, 1.0 to 1.5 mol %, 1.5 to 2.0 mol %, 1.0 mol %, or 1.5 mol %, and the lipid nanoparticle comprising the lipid-PEG conjugate in the above range may have excellent drug delivery efficiency specific to hepatocytes (or targeting hepatocytes).

According to one example, the lipid nanoparticle comprised in the composition for drug delivery to hepatocytes may comprise the ionizable lipid:phospholipid:cholesterol: lipid-PEG conjugate in the range described above or at a molar ratio of 20 to 50:10 to 30:30 to 60:0.5 to 5, at a molar ratio of 25 to 45:10 to 25:40 to 50:0.5 to 3, at a molar ratio of 25 to 45:10 to 20:40 to 55:0.5 to 3, or at a molar ratio of 25 to 45:10 to 20:40 to 55:1.0 to 1.5. The lipid nanoparticle comprising components at the molar ratio in the above range may have excellent drug delivery efficiency specific to hepatocytes (or targeting hepatocytes).

In one example, the composition for drug delivery comprising (1) the lipid nanoparticle; and (2) anionic drug, nucleic acid or combination thereof may be a composition for drug delivery into LSEC.

When the diameter of the lipid nanoparticle comprised in the composition for drug delivery into LSEC is similar to or slightly smaller than the diameter of the fenestrae, the drug delivery effect into LSEC may be excellent. In one example, the diameter of the lipid nanoparticle comprised in the composition for drug delivery into LSEC may be 20 to 200 nm, 20 to 180 nm, 40 to 180 nm, 40 to 170 nm, 50 to 160 nm, 70 to 180 nm, 70 to 170 nm, 75 to 170 nm, 75 to 165 nm, 70 to 150 nm, 70 to 130 nm, 75 to 130 nm, 80 to 120 nm, 85 to 120 nm, about 90 to 120 nm, 90 to 110 nm, 80 to 110 nm, 80 to 100 nm, 85 to 95 nm, about 90 nm, or 90 nm.

According to one example, the lipid nanoparticle comprised in the composition for drug delivery into LSEC may comprise the lipid-PEG conjugate in an amount of 0.1 to 15 mol %, 0.25 to 15 mol %, 0.5 to 15 mol %, 1 to 15 mol %, 1.5 to 15 mol %, 2 to 15 mol %, 2.5 to 15 mol %, 0.1 to 12.5 mol %, 0.25 to 12.5 mol %, 0.5 to 12.5 mol %, 1 to 12.5 mol %, 1.5 to 12.5 mol %, 2 to 12.5 mol %, 2.5 to 12.5 mol %, 0.1 to 10 mol %, 0.25 to 10 mol %, 0.5 to 10 mol %, 1 to 10 mol %, 1.5 to 10 mol %, 2 to 10 mol %, 2.5 to 10 mol %, 0.1 to 7.5 mol %, 0.25 to 7.5 mol %, 0.5 to 7.5 mol %, 1 to 7.5 mol %, 1.5 to 7.5 mol %, 2 to 7.5 mol %, 2.5 to 7.5 mol %, 0.1 to 5 mol %, 0.25 to 5 mol %, 0.5 to 5 mol %, 1 to 5 mol %, 1.5 to 5 mol %, 2 to 5 mol %, 2.5 to 5 mol %, 0.1 to 3 mol %, 0.25 to 3 mol %, 0.5 to 3 mol %, 1 to 3 mol %, 1.5 to 3 mol %, 2 to 3 mol %, 2.5 to 3 mol %, 0.1 to 2.5 mol %, 0.25 to 2.5 mol %, 0.5 to 2.5 mol %, 1 to 2.5 mol %, 1.5 to 2.5 mol %, 2 to 2.5 mol %, 0.1 to 4.5 mol %, 0.25 to 4.5 mol %, 0.5 to 4.5 mol %, 1 to 4.5 mol %, 1.5 to 4.5 mol %, 2 to 4.5 mol %, 2.5 to 4.5 mol %, 0.1 to 4 mol %, 0.25 to 4 mol %, 0.5 to 4 mol %, 1 to 4 mol %, 1.5 to 4 mol %, 2 to 4 mol %, 2.5 to 4 mol %, 0.1 to 3.5 mol %, 0.25 to 3.5 mol %, 0.5 to 3.5 mol %, 1 to 3.5 mol %, 1.5 to 3.5 mol %, 2 to 3.5 mol %, 2.5 to 3.5 mol %, 0.1 to 2.0 mol %, 0.1 to 1.5 mol %, 0.1 to 1.0 mol %, 0.5 to 2.0 mol %, 0.5 to 1.5 mol %, 0.5 to 1.0 mol %, 1.0 to 2.0 mol %, 1.0 to 1.5 mol %, 1.5 to 2.0 mol %, 1.0 mol %, or 1.5 mol %, and the lipid nanoparticle comprising the lipid-PEG conjugate in the above range may have excellent drug delivery efficiency specific to LSEC (or targeting LSEC).

According to one example, the lipid nanoparticle comprised in the composition for drug delivery into LSEC may comprise the ionizable lipid:phospholipid:cholesterol:lipid-PEG conjugate in the range described above or at a molar ratio of 20 to 50:10 to 30:30 to 60:0.5 to 5, at a molar ratio of 25 to 45:10 to 25:40 to 50:0.5 to 3, at a molar ratio of 25 to 45:10 to 20:40 to 55:0.5 to 3, or at a molar ratio of 25 to 45:10 to 20:40 to 55:1.0 to 1.5. The lipid nanoparticle comprising components at a molar ratio in the above range may have excellent drug delivery efficiency specific to LSEC (or targeting LSEC).

The lipid nanoparticle according to one example may delivery a therapeutic agent highly efficiently into liver tissue, hepatocytes and/or LSEC through liver tissue-specific properties, and may be usefully utilized for a drug for treating liver diseases, a delivery method of a gene for treatment, and the like, and a therapeutic agent mediated by liver, which mediate this highly efficient liver tissue, hepatocytes and/or LSEC-specific lipid nanoparticle. In addition, the lipid nanoparticle according to one example forms a stable complex with a gene drug such as nucleic acid, and the like, and shows low cytotoxicity and effective cell absorption, and thus it is effective to deliver the gene drug such as nucleic acid.

The lipid nanoparticle is same as described above.

The lipid nanoparticle according to one example exhibits a positive charge under the acidic pH condition by showing a pKa of 5 to 8, 5.5 to 7.5, 6 to 7, or 6.5 to 7, and may encapsulate a drug with high efficiency by easily forming a complex with a drug through electrostatic interaction with a therapeutic agent such as a nucleic acid and anionic drug (for example, protein) showing a negative charge, and it may be usefully used as a composition for intracellular or in vivo drug delivery of a drug (for example, nucleic acid).

Herein, "encapsulation" refers to encapsulating a delivery substance for surrounding and embedding it in vivo efficiently, and the drug encapsulation efficiency (encapsulation efficiency) mean the content of the drug encapsulated in the lipid nanoparticle for the total drug content used for preparation.

The encapsulation efficiency of the anionic or nucleic acid drug of the composition for delivery may be 70% or more, 75% or more, 80% or more, 85% or more, 90% or more, 91% or more, 92% or more, 94% or more, over 80% to 99% or less, over 80% to 97% or less, over 80% to 95% or less, 85% or more to 95% or less, 87% or more to 95% or less, 90% or more to 95% or less, 91% or more to 95% or less, 91% or more to 94% or less, over 91% to 95% or less, 92% or more to 99% or less, 92% or more to 97% or less, or 92% or more to 95% or less.

According to one example, the encapsulation efficiency may be calculated by commonly used methods, and for example, the drug encapsulation efficiency may be calculated by the following Equation 2, by treating Triton-X to the lipid nanoparticle according to one example and measuring the fluorescence intensity of the Triton-X-treated and Triton-X-untreated lipid nanoparticles in a specific wavelength bandwidth (for example, excitation: 480490 nm, emission: 520530 nm).

Drug encapsulation efficiency (%)=(Fluorescence intensity(fluorescence) of the Triton-$X$-treated lipid nanoparticle−Fluorescence intensity(fluorescence) of the Triton-$X$-untreated lipid nanoparticle)/(Fluorescence intensity(fluorescence) of the Triton-$X$-treated lipid nanoparticle)×100 (Equation 2)

The composition for drug delivery according to one example may comprise Cas9 mRNA with high encapsulation efficiency. The previously known composition for delivering Cas9 mRNA has a limitation in using it as a composition for delivering Cas9 mRNA, as it comprises Cas9 mRNA at a low ratio. On the other hand, the lipid nanoparticle according to one example may comprise Cas9 mRNA with high encapsulation efficiency, specifically, encapsulation efficiency of 70% or more, and thus it may be usefully utilized for gene editing therapy.

The anionic drug may be an anionic biopolymer-drug conjugate such as various kinds of peptides, protein drugs, protein-nucleic acid structures or hyaluronic acid-peptide conjugates, hyaluronic acid-protein conjugates, which have an anion, and the like. The non-restrictive examples of the protein drugs may be apoptosis-inducing factors (e.g., cytochrome C, caspase 3/7/8/9, etc.) and including gene editing proteins such as Cas 9, cpf1 which are gene editing scissors, and various intracellular proteins (e.g., transcription factors), and the like.

The nucleic acid may be one or more kinds selected from the group consisting of small interfering RNA (siRNA), ribosome ribonucleic acid (rRNA), ribonucleic acid (RNA), deoxyribonucleic acid (DNA), complementary deoxyribonucleic acid (cDNA), aptamer, messenger ribonucleic acid (mRNA), transfer ribonucleic acid (tRNA), antisense oligonucleotide, shRNA, miRNA, ribozyme, PNA, DNAzyme and sgRNA for gene editing, and the like, but not limited thereto.

Herein, the term "siRNA" refers to double stranded RNA (duplex RNA) which can induce RNAi (RNA interference) through cleavage of specific mRNA, or single stranded RNA that has a double stranded form inside the single stranded RNA. It consists of a sense RNA strand having the sequence homologous to mRNA of a target gene and an antisense RNA strand having the sequence complementary thereto. As siRNA can inhibit expression of a target gene, it is provided by an effective gene knock-down method or method of gene therapy. Binding between double strands is carried out through hydrogen bonding between nucleotides, and not all nucleotides within the double strand must be complementary and completely bound.

The length of siRNA may be about 15 to 60, specifically about 15 to 50, about 15 to 40, about 15 to 30, about 15 to 25, about 16 to 25, about 19 to 25, about 20 to 25, or about 20 to 23 nucleotides. The siRNA length means the number of nucleotides on one side of the double stranded RNA, that is, the number of base pairs, and in case of single stranded RNA, means the length of the double strand inside the single stranded RNA. In addition, siRNA may be composed of nucleotides introduced with various functional groups for the purpose of increasing blood stability or weakening an immune response, and the like.

Herein, the term "antisense oligonucleotide" may be modified at a position of one or more bases, sugars or backbones to enhance the efficacy (De Mesmaeker et al., Curr Opin Struct Biol., 5(3):343-55, 1995). The oligonucleotide backbone may be modified by phosphorothioate, phosphotriester, methyl phosphonate, short-chain alkyl, cycloalkyl, short-chain heteroatomic, heterocyclic intersaccharide binding, and the like. In addition, the antisense oligonucleotide may comprise one or more substituted sugar moieties. The antisense oligonucleotide may comprise a modified base. The modified base includes hypoxanthine, 6-methyladenine, 5-me pyrimidine (particularly, 5-methylcytosine), 5-hydroxymethylcytosine (HMC), glycosyl HMC, gentiobiosyl HMC, 2-aminoadenine, 2-thiouracil, 2-thiothymine, 5-bromouracil, 5-hydroxymethyluracil, 8-azaguanine, 7-deazaguanine, N6(6-aminohexyl)adenine, 2,6-diaminopurine, and the like.

Herein, "single stranded deoxyribonucleic acid (ssDNA)" means a single stranded oligonucleotide which binds to specific target DNA selectively and induces an antigene effect.

Herein, "aptamer" means an oligonucleotide (generally, 20~80 nt DNA or RNA) which binds to a specific target. Preferably, herein, "aptamer" means an oligonucleotide aptamer (e.g., DNA or RNA aptamer).

Herein, "mRNA" means synthetic mRNA (in vitro transcribed mRNA) capable of expressing a gene.

Herein, "shRNA" means single-stranded 50 to 70 nucleotides, and forms a stem-loop (stemloop) structure in vivo. On both sides of the loop of 5 to 10 nucleotides, complementarily, long RNA of 19 to 29 nucleotides is base-paired to form a double-stranded stem.

Herein, "miRNA (microRNA)" means a single stranded RNA molecule which controls gene expression and consists of full length 21 to 23 nucleotides. miRNA is an oligonucleotide which is not expressed in a cell, and has a short stem-loop structure. miRNA has full or partial homology with one or two or more mRNA (messenger RNA) and suppresses target gene expression through complementary binding to the mRNA.

Herein, "ribozyme" is a kind of RNA, and is RNA which recognizes a nucleotide sequence of specific RNA and has the same function as enzyme cutting it by itself. The ribozyme is a complementary nucleotide sequence of a target messenger RNA strand and consists of a region that binds with specificity and a region that cuts the target RNA.

Herein, "DNAzyme" is a single stranded DNA molecule having enzyme activity, and DNAzyme consisting of 10 to 23 nucleotides (10-23 DNAzyme) cuts a RNA strand at a specific position under the physiologically similar condition. The 10-23 DNAzyme cuts between any exposed purines and pyrimidines without base pairing. The 10-23 DNAzyme consists of an active site (catalytic domain) of enzyme consisting of 15 conserved nucleotide sequences (for example, 5'-GGCTAGCTACAACGA-3') and an RNA substrate binding domain consisting of 7-8 DNA nucleotide sequences which recognize RNA substrates to the left and right of the active domain of the enzyme afore-described.

Herein, "PNA (Peptide nucleic acid)" is a molecule having all properties of nucleic acids and proteins, and means a molecule capable of complementarily binding to DNA or RNA. The PNA was first reported in 1999 as similar DNA in which nucleobases are linked by peptide bonds (document [Nielsen P E, Egholm M, Berg R H, Buchardt O, "Sequence-selective recognition of DNA by strand displacement with a thymine-substituted polyamide", Science 1991, Vol. 254: pp 1497-1500]). The PNA is not found in the natural world and is artificially synthesized by a chemical method. The PNA causes a hybridization reaction with a natural nucleic acid of a complementary nucleotide sequence to form a double strand. PNA/DNA double strands are more stable than DNA/DNA double strands for the same length. As a backbone of peptides, N-(2-aminoethyl)glycine repeatedly linked by amide bonds is most commonly used, and in this case, the backbone of the peptide nucleic acid is electrically neutral different from the backbone of the natural nucleic acid. 4 nucleotides present in PNA have almost the same spatial size and distance between nucleotides as in case of the natural nucleic acid. The PNA is not only chemically more stable than the natural nucleic acid, but also biologically stable because it is not degraded by nuclease or protease.

Herein, "sgRNA" is an oligonucleotide (generally, RNA molecule) binding to a specific DNA target, and means a complex single RNA molecule of crispr RNA (crRNA) and tracer (tracrRNA). It is an RNA molecule which is used for recognizing a specific DNA sequence with Cas9 nuclease in the CRISPR system and enables selective gene cleavage, and approximately, comprises a 20-nt sequence capable of complementarily binding to DNA, and has a total length of 100 nt.

Herein, "gene editing protein" refers to Cas9, spCas9, cjCas9, casX, CasY and Cpf1, and the like, and refers to a protein that recognizes a target DNA nucleotide sequence with sgRNA to cause DNA cleavage.

The target cell to which a drug and/or nucleic acid is delivered by the lipid nanoparticle according to one example may be a hepatocyte and/or LSEC in vivo or isolated in vivo. The composition for drug delivery and/or complex of the drug (anionic drug, nucleic acid or combination thereof) and lipid nanoparticle according to one example may target or specifically target a hepatocyte and/or LSEC. Accordingly, the lipid nanoparticle or composition for drug or nucleic acid delivery comprising the lipid nanoparticle according to one example may be for treatment of acute or chronic liver diseases such as hepatic fibrosis, liver cirrhosis, hepatitis (e.g., hepatitis A, hepatitis B, hepatitis C, etc.), and in addition, it may be utilized as a composition for delivery of a therapeutic agent (drug) absorbed through liver.

Other aspect provides a pharmaceutical composition for preventing or treating liver disease, comprising (1) the lipid nanoparticle; and (2) an anionic drug, nucleic acid or combination thereof.

The lipid nanoparticle comprised in the pharmaceutical composition for preventing or treating liver disease is same as the lipid nanoparticle comprised in the composition for drug delivery afore-mentioned.

The anionic drug and nucleic acid comprised in the pharmaceutical composition for preventing or treating liver disease is same as the anionic drug and nucleic acid comprised in the composition for drug delivery afore-mentioned.

The pharmaceutical composition for preventing or treating liver disease according to one example may comprise a lipid nanoparticle in which an anionic drug and/or nucleic acid is encapsulated.

The liver disease may be one or more kinds selected from the group consisting of ATTR amyloidosis, hypercholesterolemia, hepatitis B virus infection, acute liver failure, cirrhosis, and liver fibrosis.

The anionic drug may have an effect for preventing or treating liver disease.

The nucleic acid may have an effect for preventing or treating liver disease, and for example, it may be siRNA and/or miRNA which can inhibit expression such as (1) TTR (Transthyretin) ((e.g., human TTR (protein: GenBank Accession Nos. NP_000362.1; gene: GenBank Accession Nos. NM_000371.4, etc.), mouse TTR (protein: GenBank Accession No.; NP_038725.1; gene: GenBank Accession No. NM_013697.5, etc.)), (2) PCSK9 (Proprotein convertase subtilisin/kexin type 9) ((e.g., human PCSK9 (protein: GenBank Accession Nos. NP_777596.2; gene: GenBank Accession Nos. NM_174936.4, etc.), mouse PCSK9 (protein: GenBank Accession No. NP_705793.1; gene: GenBank Accession No. NM_153565.2, etc.)), (3) HBV (Hepatitis B Virus) (e.g., HBV genotype A (e.g., GenBank Accession No.: X02763, X51970, or AF090842); HBV genotype B (e.g., GenBank Accession No.: D00329, AF100309, or AB033554); HBV genotype C (e.g., GenBank Accession No.: X04615, M12906, AB014381, AB042285, AB042284, AB042283, AB042282, AB026815, AB026814, AB026813, AB026812, or AB026811); HBV genotype D (e.g., GenBank Accession No.: X65259, M32138, or X85254); HBV genotype E (e.g., GenBank Accession No.: X75657 or AB032431); HBV genotype F (e.g., GenBank Accession No.: X69798, AB036910, or AF223965); HBV genotype G (e.g., GenBank Accession No.: AF160501, AB064310, or AF405706) HBV genotype H (e.g., AY090454, AY090457, or AY090460) (4) Bax (BCL2 associated X)) ((e.g., human Bax (protein: GenBank Accession Nos. NP_001278357.1, NP_001278358.1, NP_001278359.1, NP_001278360.1, NP_004315.1; gene: GenBank Accession Nos. NM_001291428.2, NM_001291429.2, NM_001291430.1, NM_001291431.2, NM_004324.4, etc.), mouse Bax (protein: GenBank Accession No. NP_031553.1; gene: GenBank Accession No. NM_007527.3, etc.), (5) VEGF (Vascular endothelial growth factor) (e.g., VEGFA ((e.g., human VEGFA (protein: GenBank Accession Nos. NP_001020537.2, NP_001020538.2, NP_001020539.2, NP_001020540.2, NP_001020541.2; gene: GenBank Accession Nos. NM_003376.6, NM_001025366.3, NM_001025367.3, NM_001025368.3, NM_001025369.3, etc.), mouse VEGFA (protein: GenBank Accession No. NP_001020421.2, NP_001020428.2, NP_001103736.1, NP_001103737.1, NP_001103738.1; gene: GenBank Accession No. NM_001025250.3, NM_001025257.3, NM_001110266.1, NM_001110267.1, NM_001110268.1, etc.); VEGFB ((e.g., human VEGFB (protein: GenBank Accession Nos. NP_001230662.1, NP_003368.1; gene: GenBank Accession Nos. NM_003377.5, NM_001243733.2, etc.), mouse VEGFB (protein: GenBank Accession No. NP_001172093.1, NP_035827.1; gene: GenBank Accession No. NM_001185164.1, NM_011697.3, etc.); VEGFC (e.g., human VEGFC (protein: GenBank Accession Nos. NP_005420.1; gene: GenBank Accession Nos. NM_005429.5, etc.), mouse VEGFC (protein: GenBank Accession No.; NP_033532.1; gene: GenBank Accession No. NM_009506.2, etc.)), and/or (6) PDGF (Platelet-derived growth factor) (e.g., PDGFA ((e.g., human PDGFA (protein: GenBank Accession Nos. NP_002598.4, NP_148983.1; gene: GenBank Accession Nos. NM_002607.5, NM_033023.4, etc.), mouse PDGFA (protein: GenBank Accession No. NP_032834.1, NP_001350200.1; gene: GenBank Accession No. NM_008808.4, NM_001363271.1, etc.)); PDGFB ((e.g., human PDGFB (protein: GenBank Accession Nos. NP_002599.1, NP_148937.1; gene: GenBank Accession Nos. NM_033016.3, NM_002608.4, etc.), mouse PDGFB (protein: GenBank Accession No. NP_035187.2; gene: GenBank Accession No. NM_011057.4, etc.)); PDGFC ((e.g., human PDGFC (protein: GenBank Accession Nos. NP_057289.1; gene: GenBank Accession Nos. NM_016205.3, etc.), mouse PDGFC (protein: GenBank Accession No. NP_064355.1, NP_001344675.1; gene: GenBank Accession No. NM_019971.3, NM_001357746.1, etc.)); PDGFD (e.g., human PDGFD (protein: GenBank Accession Nos. NP_079484.1, NP_149126.1; gene: GenBank Accession Nos. NM_033135.4, NM_025208.5, etc.), mouse PDGFD (protein: GenBank Accession No. NP_082200.1, NP_001344326.1, NP_001344327.1; gene: GenBank Accession No. NM_027924.3, NM_001357397.1, NM_001357398.1, etc.)).

The pharmaceutical composition may be administered by various routes including parenteral administration into mammals including humans, and parenteral administration may be applied intravenously, subcutaneously, intraperitoneally or locally, and the dosage varies depending on the condition and body weight of the patient, degree of disease, drug form, administration route and time, but may be appropriately selected by those skilled in the art.

When the pharmaceutical composition according to one example is formulated, it is prepared by using a diluent or excipient such as a filler, an extender, a binding agent, a wetting agent, a disintegrant, a surfactant, and the like used commonly.

The formulation for parenteral administration includes a sterilized aqueous solution, a non-aqueous solvent, a suspended solvent, emulsion, a lyophilized formulation, a suppository, and the like.

As the non-aqueous solvent and suspended solvent, propylene glycol, polyethylene glycol, plant oil such as olive oil, injectable ester such as ethyl oleate, and the like may be used. As a base compound of the suppository, witepsol, macrogol, tween 61, cacao butter, laurin butter, glycerol, gelatin, and the like.

The pharmaceutical composition according to one example is administered in a pharmaceutically effective dose. Herein, "pharmaceutically effective dose" means an amount sufficient to treat disease at a reasonable benefit/risk ratio applicable to medical treatment, and the effective dose level may be determined depending on factors including the patient's disease type, severity, drug activity, drug sensitivity, administration time, administration route and excretion rate, treatment period and concomitant drugs, and other factors well known in the medical field. The pharmaceutical composition according to one example may be administered as an individual therapeutic agent or may be administered in combination with other therapeutic agents, and may be administered sequentially or simultaneously with conventional therapeutic agents, and may be singly or multiply administered. It is important to administer an amount capable of obtaining the maximum effect with a minimum amount without side effects, in consideration of all of the above factors, and this may be easily determined by those skilled in the art.

Specifically, the effective dose of the compound according to the present invention may vary depending on the patient's age, gender and body weight, and may be administered daily or every other day, or administered by dividing into 1 to 3 times a day. However, it may be increased or reduced depending on the administration route, severity of obesity, gender, body weight, age, and the like, and therefore, the above dose does not limit the scope of the present invention in any way.

(128) In one specific example, the pharmaceutical composition may be administered in a dose of 0.1 to 100 mg/kg, 0.1 to 50 mg/kg, 1 to 10 mg/kg, or 1 to 5 mg/kg, based on the concentration of the drug (anionic drug, nucleic acid or combination thereof) comprised in the pharmaceutical composition.

Other aspect provides a method for prevention or treatment of liver disease comprising administering a composition (for example, the pharmaceutical composition for preventing or treating liver disease), comprising (1) the lipid nanoparticle; and (2) an anionic drug, nucleic acid or combination thereof. The lipid nanoparticle, anionic drug, nucleic acid, pharmaceutical composition and liver disease are same as described above.

According to one example, the method for prevention or treatment of liver disease may further comprise confirming (selecting) a patient in need of prevention and/or treatment of the liver disease, before administering the composition.

A subject to which the method for treatment is applied means a mammal including mice, livestock, and the like, including humans who have or may have liver disease, but not limited thereto. The pharmaceutical composition comprising the lipid nanoparticle according to one example can effectively deliver the anionic drug and/or nucleic acid to liver, and thus it may treat the subject effectively.

According to one example, a method for prevention or treatment of liver disease, comprising administering a pharmaceutically effective dose of composition (for example, the pharmaceutical composition for preventing or treating liver disease), comprising (1) the lipid nanoparticle; and (2) an anionic drug, nucleic acid or combination thereof to a patient may be provided. The pharmaceutically effective dose is same as described above, and a suitable total daily amount may be determined by treatment within the scope of correct medical judgement, and may be administered once or divided into several times. However, a specific therapeutically effective dose for a particular patient will be applied differently depending on various factors including the specific composition, the patient's age, body weight, general health condition, gender and diet, administration time, administration route and excretion rate of the composition, treatment period, and drugs used together or concurrently with the specific composition, in addition to the type and extent of the response to be achieved, and whether or not other agent is used, if necessary, and similar factors well known in the pharmaceutical field.

Advantageous Effects

According to one example, the lipid nanoparticle is liver tissue-specific, have excellent biocompatibility and can deliver a gene therapeutic agent with high efficiency, and thus it can be usefully used in related technical fields such as lipid nanoparticle mediated gene therapy.

BRIEF DESCRIPTION OF THE DRAWINGS

FIG. 4a shows the luminescence intensity measured by transforming LNP encapsulating mRNA (luc mRNA) encoding luciferase into HeLa cell and then dissolving the cell, and FIG. 4b shows the luminescence intensity measured by transforming LNP encapsulating luc mRNA to a hepatocyte and then dissolving the cell. In FIG. 4b, +ApoE refers to a group treated by ApoE3, and -ApoE refers to a group untreated by ApoE3.

MODE FOR INVENTION

Figure 1A:
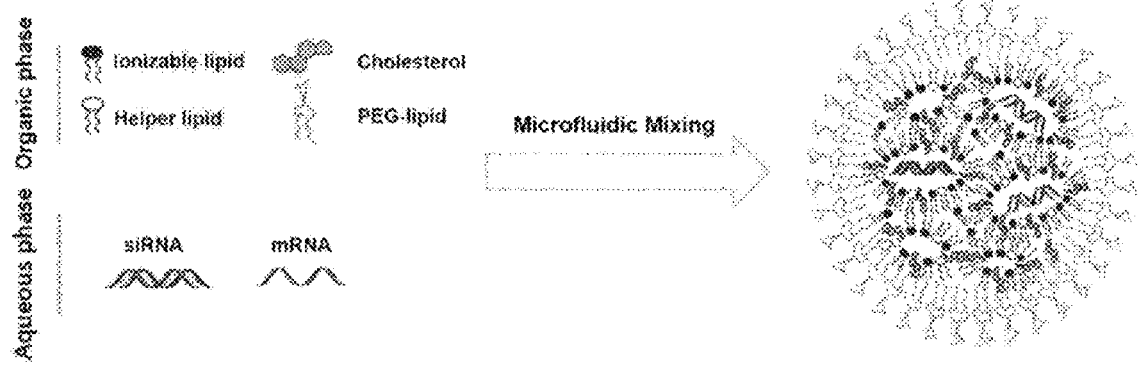
FIG. 1a shows an exemplary structure of the lipid nanoparticle according to one example.

The present invention will be described in more detail by the following examples, but the scope is not intended to be limited by the following examples.

Hereinafter, the present invention will be described in more detail by examples. These examples are only for describing the present invention in more detail, and it will be apparent to those skilled in the art that the scope of the present invention is not limited by these examples according to the gist of the present invention.

Example 1. Preparation of Ionizable Lipids

Example 1-1. Preparation of Ionizable Lipids

Ionizable lipids were synthesized by reacting the amine-based compounds of Table 1 below comprising a 6-membered heterocyclic tertiary amine and 1,2-epoxydodecane (hereinafter, C10) (Sigma-Aldrich, USA) at a molar ratio of 1:n (n=primary amine×2+secondary amine×1).

TABLE 1

| Name | Chemical formula |
|---|---|
| 241 | (piperidine-propyl-NH₂ structure) |
| 242 | (4-aminomethyl-1-methylpiperidine structure) |
| 243 | (aminoethyl-methylpiperazine structure) |
| 244 | (piperazine-ethyl-NH₂ structure) |
| 245 | (piperazine-propyl-NH₂ structure) |
| 246 | (bis-aminopropyl piperazine structure) |

Specifically, each of 241 to 246 amines of the Table 1 and epoxide (C10) were added at a molar ratio of 1:n (n=primary amine×2+secondary amine×1) in a 5 ml vial with a magnetic bar and reacted in a stirrer at 750 rpm, 90° C. for 3 days. Then, after purifying with WELUX fine silica column (Intertec, Korea), the molecular weight of each ionizable lipid produced by the reaction was calculated and they were stored at a concentration of 100 mg/ml using ethanol. The ionizable lipid produced by using 241 amine and C10 was named '241-C10', and other ionizable lipids produced by using other kinds of amines were named 'used amine name (241 to 246)-C10' in the same way.

Example 1-2. Confirmation of Produced Ionizable Lipids

In order to confirm the ionizable lipids produced in the Example 1-1, 1H NMR was performed. Specifically, the ionizable lipid (246-C10) synthesized in Example 1-1 of 5 ug was prepared by diluting in CDCl.sub.3 (sigma, USA) 0.5 ml to 100 mmole concentration. Then, 0.5 ml each was put into a tube for 400 MHz NMR and the top was sealed, and then sealed with parafilm to obtain NMR spectra using Agilent 400 MHZ FT-NMR (Agilent, USA), and the result shows that the signal representing each functional group of 246-C10 was saturated.

In addition, in order to confirm the ionizable lipids (241-C10 to 246-C10) prepared in Example 1-1, MS analysis was performed. Specifically, the ionizable lipids were diluted in ethanol at a concentration of 0.5 ppm or less and MS analysis was performed. The equipment used for the analysis was 6230 LC/MS of Agilent Technologies (Palo Alto, USA) and the Zorbax SB-C18 (100 mm×2.1 mm i.d., 3.5 μm) of Agilent Technologies was used for the separation tube, and two solvents of distilled water (A) containing 0.1% formic acid and acetonitrile (B) were gradient eluted. The solvent gradient of the mobile phase was maintained for 4 minutes until the ratio of the organic solvent acetonitrile (B) was initially increased from 30% to 80% for 2 minutes and then the ratio of the organic solvent was lowered to 30% again and stabilized. The flow rate of the mobile phase was 300 μl/min, and then, the injection volume of the analyzer was 2 μl. The result of performing the MS analysis was shown in Table 2 below. As shown in Table 2, it could be confirmed that the measured m/z ratio and calculated m/z ratio of the ionizable lipids were almost identical.

TABLE 2

| | Chemical formula | Calculated m/z ratio | Observed m/z ratio |
|---|---|---|---|
| 241-C10 | $C_{32}H_{66}N_2O_2$ | 510.87864 | 511.5201 |
| 242-C10 | $C_{31}H_{64}N_2O_2$ | 496.85206 | 497.5043 |
| 243-C10 | $C_{31}H_{65}N_3O_2$ | 511.8667 | 513.5186 |
| 244-C10 | $C_{42}H_{87}N_3O_3$ | 682.15848 | 682.6821 |
| 245-C10 | $C_{43}H_{89}N_3O_3$ | 696.18506 | 696.7045 |
| 246-C10 | $C_{58}H_{120}N_4O_4$ | 937.5978 | 937.9383 |

From the result, it could be confirmed that the ionizable lipids were well made in Example 1.1.

Example 2. Preparation of Lipid Nanoparticles

Example 2-1. Preparation of Lipid Nanoparticles

The ionizable lipids (241-C10 to 246-C10) prepared in the Example 1-1, cholesterol (Cholesterol powder, BioReagent, suitable for cell culture, ≥99%, sigma, Korea), phospholipid (DSPC) (Avanti, US), and a lipid-PEG conjugate (ceramide- PEG conjugate; C16 PEG2000 Ceramide, Avanti, US) were dissolved in ethanol at a molar ratio of 42.5:13:43:1.5.

The ethanol in which the ionizable lipids, cholesterol, phospholipid and lipid-PEG were dissolved and acetate buffer were mixed with a microfluid mixing device (Benchtop Nanoassemblr; PNI, Canada) at a flow rate of 12 ml/min in a volume ratio of 1:3, thereby preparing lipid nanoparticles (LNPs).

Example 2-2. Preparation of Nucleic Acid-Encapsulated Lipid Nanoparticles

The ionizable lipids (241-C10 to 246-C10) prepared in the Example 1-1, cholesterol (Cholesterol powder, BioReagent, suitable for cell culture, ≥99%, sigma, Korea), phospholipid (DSPC or DOPE) (18:0 PC (DSPC), 18:1 (49-Cis) PE (DOPE), Avanti, US), and a lipid-PEG conjugate (ceramide-PEG conjugate; C16 PEG2000 Ceramid, Avanti, US) were dissolved in ethanol. An RNA therapeutic agent, mRNA (luciferase mRNA; SEQ ID NO: 1) 30 ug was diluted in sodium citrate 0.75 ml, or siRNA (siFVII; SEQ ID NOs: 2 and 3 were mixed at the same molar ratio, or siFVIII; SEQ ID NOs: 4 to 11 were mixed at the same molar ratio, or siLuc: SEQ ID NOs: 12 and 13 were mixed at the same molar ratio) 30 ug was diluted in sodium acetate (50 mM) 0.75 ml to prepare an aqueous phase.

The used siRNA sequences are as follows: SEQ ID NO: 2 (FVII target siRNA_sense; 5'-GGAUCAUCUCAAGUC-UUACdtdt-3'), SEQ ID NO: 3 (FVII target siRNA_antisense; 5'-GUAAGACUUGAGAUGAUCCdtdt-3'), SEQ ID NO: 4 (FVIII target siRNA_sense_1; 5'CUUAUAUCGUGGAGAAUUAdtdt-3') SEQ ID NO: 5 (FVIII target siRNA_antisense_1; 5'-UAAUUCUC-CACGAUAUAAGdtdt-3'), SEQ ID NO: 6 (FVIII target siRNA_sense_2; 5'-UCAAAGGAUUCGAUGGUAUdtdt-3'), SEQ ID NO: 7 (FVIII target siRNA_antisense_2; 5'-AUACCAUCGAAUCCUUUGAdtdt-3'), SEQ ID NO: 8 (FVIII target siRNA_sense_3; 5'-CAAGAGCAC-UAGUGAUUAUdtdt-3'), SEQ ID NO: 9 (FVIII target siRNA_antisense_3; 5'-AUAAUCACUAGUGCUCUUGdtdt-3'), SEQ ID NO: 10 (FVIII target siRNA_sense_4; 5'-GGGCACCACUCCUGAAAUAdtdt-3'), SEQ ID NO: 11 (FVIII target siRNA_antisense_4; 5'-UAUUUCAG-GAGUGGUGCCCdtdt-3'), SEQ ID NO: 12 (siLuc_sense; 5'-AACGCUGGGCGUUAAUCAAdtdt-3'), SEQ ID NO: 13 (siLuc_antisense; 5'-UUGAUUAACGCCCAGCGU-Udtdt-3').

The aqueous phase (sodium acetate or sodium citrate) in which the organic phase (ethanol) in which the ionizable lipids, cholesterol, phospholipid and lipid-PEG conjugate (hereinafter, lipid-PEG) were dissolved and an RNA therapeutic agent (nucleic acid) were dissolved were mixed through a microfluid mixing device (Benchtop Nanoassemblr; PNI, Canada) at a flow rate of 12 ml/min, to prepare lipid nanoparticles (LNPs) in which the nucleic acid was encapsulated. (i) In order to prepare a lipid nanoparticle in which mRNA is encapsulated, the ionizable lipid:phospholipid (DOPE):cholesterol:lipid-PEG (C16-PEG2000 ceramide) were dissolved in ethanol at a molar ratio of 26.5:20:52.5 to 51:1.0 to 2.5 (adjusting the content of cholesterol and lipid-PEG so that the total sum of the molar ratio is 100), and the organic phase and the aqueous phase were mixed so that the mRNA (luciferase mRNA; SEQ ID NO:1):ionizable lipid was at the weight ratio of 1:10, and thereby a lipid nanoparticle was prepared. (ii) In order to prepare a lipid nanoparticle in which siRNA is encapsulated, the ionizable lipid:phospholipid (DSPC):cholesterol:lipid-PEG (C16-PEG2000 ceramide) were dissolved in ethanol at a molar ratio of 42.5:13:44 to 39.5:0.5 to 5.0 (adjusting the content of cholesterol and lipid-PEG so that the total sum of the molar ratio is 100), and the organic phase and the aqueous phase were mixed so that the siRNA (siFVII; SEQ ID NOs: 2 and 3 were mixed at the same molar ratio, or siFVIII; SEQ ID NOs: 4 to 11 were mixed at the same molar ratio, or siLuc: SEQ ID NOs: 12 and 13 were mixed at the same ratio): ionizable lipid was at the weight ratio of 1:7.5 and thereby a lipid nanoparticle (LNP) was prepared.

The prepared LNPs were dialyzed against PBS for 16 hours using a 3500 MWCO dialysis cassette to remove ethanol and adjust the body pH and the pH of the nanoparticles.

The lipid nanoparticles comprising the ionizable lipid '241-C10' were named '241-C10 LNP', and the lipid nanoparticles prepared by using the ionizable lipid comprising amine (including lipid nanoparticles in which a nucleic acid was encapsulated) were named 'comprised amine name (214 to 246)-C10 LNP'.

Example 2-3. Observation of Nucleic Acid-Encapsulated Lipid Nanoparticles

Figure 1B:
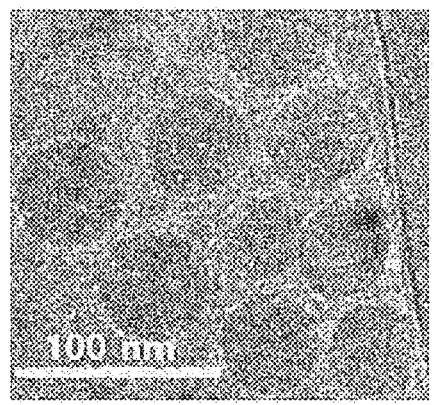
FIG. 1B shows an image of observing the nanoparticle according to one example by Cryo-TEM.

(26) The Lipid nanoparticles in which siLuc (SEQ ID NOs: 12 and 13) were encapsulated was prepared by using a ceramide-PEG conjugate (C16-PEG2000 ceramide) as Example 2-2. The prepared lipid nanoparticles (comprising 1.5 mol % of ceramide-PEG conjugate) were loaded on 200 mesh carbon lacey film Cu-grid in an amount of 60 ug based on siRNA concentration and were immersed in ethane liquefied with vitrobot (about −170 degrees or less) and were plunge frozen to be prepared, and then were observed with Cryo-TEM (Tecnai F20, FEI), and the result was shown in FIG. 1B. As shown in FIG. 1B, spherical particles with a solid shape were observed.

Example 3. pKa of Lipid Nanoparticles

In the present example, pKa of each lipid nanoparticle (LNP) formulated in the Example 2-1 was calculated through In vitro TNS assay. Anionic TNS becomes lipophilic by interacting with a positively charged ionizable lipid, and as the pH value becomes close to the pKa value of each LNP, the lipophilic property of TNS becomes lower and more water molecules quench the TNS fluorescence, and therefore, lipid nanoparticles having a pKa of 6.0 to 7.0 have excellent in vivo drug delivery efficiency, and lipid nanoparticles showing a "s-type curve" in the graph representing fluorescence according to pH mean that they are easy to interact with the endosome membrane and can easily escape the endosome during acidification.

Figure 2:
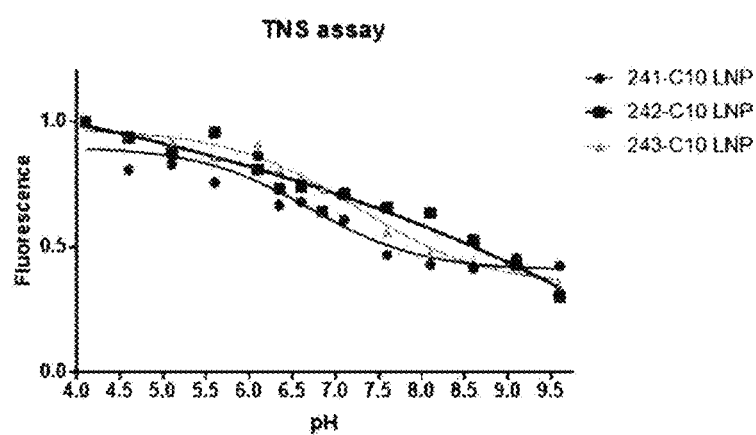
FIG. 2 (241-C10 LNP to 243-C10 LNP) and FIG. 3 (244-C10 LNP to 246-C10 LNP) show the result of measuring the fluorescence intensity shown by each lipid nanoparticle in a solution having a range of pH 4.1 to pH 9.6.
Figure 3:
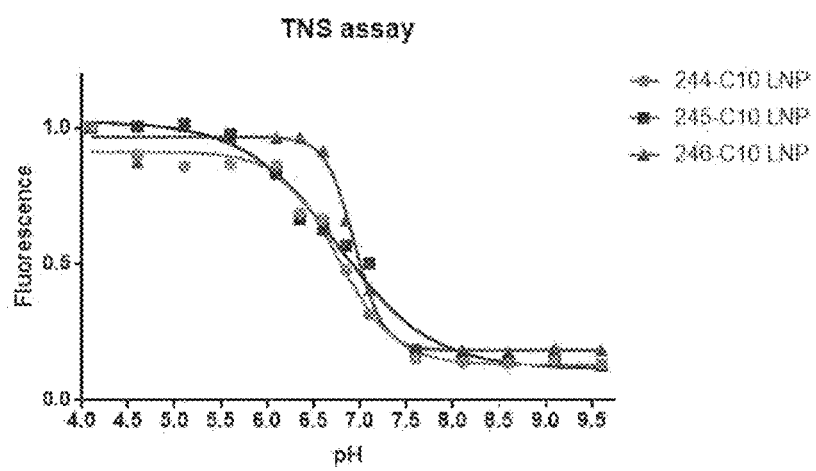

Specifically, the pH of the solution comprising 20 mM sodium phosphate, 25 mM citrate, 20 mM ammonium acetate, and 150 mM NaCl with 0.1N NaOH and/or 0.1N HCl at an interval of 0.5 from pH 4.1 to pH 9.6 to prepare solutions of various pH units. 100 μl of each solution having each pH (pH with an interval of 0.5 from pH 4.1 to pH 9.6) was added to a black 96 well plate and each was added to a solution having the pH in the range so as to be the final concentration of 6 uM using a TNS stock solution of 300 uM. 241-C10 LNP to 246-C10 LNP were added to the mixed solution so that the final concentration is 20 uM. The fluorescence intensity was measured by excitation at 325 nm and emission at 435 nm through a Tecan equipment, and the fluorescence intensity for each lipid nanoparticle was shown in FIG. 2 and FIG. 3, and the pKa for each lipid nanoparticle was calculated as a pH value reaching half of the maximum fluorescence and shown in Table 3 below. As shown in FIG. 3, it could be seen that 244-C10 LNP to 246-C10 LNP exhibit a fluorescence titration s-shaped curve through non-linear regression.

TABLE 3

| Lipid nanoparticle | pKa |
| --- | --- |
| 241-C10 LNP | 7.7 |
| 242-C10 LNP | 8.7 |
| 243-C10 LNP | 8.2 |
| 244-C10 LNP | 6.8 |
| 245-C10 LNP | 6.9 |
| 246-C10 LNP | 7 |

As confirmed in the Table 3, it was confirmed that the lipid nanoparticles according to one example showed pKa 6.0 to 7.0 range in which in vivo safety and drug release are excellent.

The LNPs in which a nucleic acid was encapsulated, prepared by the method as Example 2-2, also showed the same pattern according to the type of ionizable lipids contained (type of amine contained in the ionizable lipids).

Example 4. Confirmation of Characteristics of Lipid Nanoparticles

Example 4-1. Particle Size Measurement

In the present example, the size of the lipid nanoparticles (LNP; comprising 1.5 mol % of lipid-PEG) in which mRNA was encapsulated measured in Example 2-2 was to be measured. It was diluted using PBS so that the concentration of RNA (luciferase mRNA; SEQ ID NO: 1) comprised in each lipid nanoparticle prepared in Example 2-2 was 1 ug/ml, and the diameter and polydispersity index (PDI) of the LNPs were measured using dynamic light scattering (DLS) in Malvern Zetasizer Nano (Malvern Instruments, UK), and the result was described in Table 4 below.

TABLE 4

| Lipid nanoparticle | Diameter (nm) | PDI |
| --- | --- | --- |
| 241-C10 LNP | 128 | 0.259 |
| 242-C10 LNP | 77 | 0.210 |
| 243-C10 LNP | 56 | 0.225 |
| 244-C10 LNP | 66 | 0.149 |
| 245-C10 LNP | 70 | 0.210 |
| 246-C10 LNP | 68 | 0.143 |

As confirmed in the Table 4, the lipid nanoparticles according to one example showed the particle size that is easy to be introduced into hepatocytes and has excellent drug release, and it could be found that the PDI values were small and the particles were uniform in order of 241-C10 LNP>243-C10 LNP>242-C10 LNP=245-C10 LNP>244-C10 LNP>246-C10 LNP.

Example 4-2. Measurement of Encapsulation Efficiency

The encapsulation efficiency (drug encapsulation efficiency, %) of each LNP (comprising 1.5 mol % of lipid-PEG) in which siRNA (siFVII siRNA) was encapsulated as a nucleic acid drug was measured through Ribogreen analysis (Quant-iT™ RiboGreen® RNA, Invitrogen). The LNPs in which a nucleic acid drug was encapsulated prepared in the Example 2-2 were diluted with 1×TE buffer solution 500 in a 96 well plate so that the final concentration of siRNA was 4-7 ug/ml. To the group untreated with Triton-X (Triton-x LNP(−)), 1× TE buffer 50 μl was added, and to the group treated with Triton-X (Triton-x LNP(+)), 2% Triton-X buffer 50 μl was added. By incubating at 37° C. for 10 minutes, the nucleic acid encapsulated by degrading LNPs with Triton-X was released. Then, Ribogreen reagent 100 μl was added to each well. The fluorescence intensity (FL) of Triton LNP(−) and Triton LNP(+) was measured by the wavelength bandwidth (excitation: 485 nm, emission: 528 nm) in Infinite® 200 PRO NanoQuant (Tecan), and the drug encapsulation efficiency (encapsulation efficiency, %) was calculated as the following Equation 3. The drug encapsulation efficiency (%) for each LNP was shown in Table 5 below as the average value of the results measured repeatedly twice.

$$\text{Drug encapsulation efficiency (\%)} = (\text{Fluorescence intensity of Triton } LNP(+) - \text{Fluorescence intensity of Triton } LNP(-))/(\text{Fluorescence intensity of Triton } LNP(+)) \times 100 \quad \text{(Equation 3)}$$

TABLE 5

| Lipid nanoparticle | Encapsulation efficiency (%) |
| --- | --- |
| 241-C10 LNP | 84 |
| 242-C10 LNP | 83 |
| 243-C10 LNP | 91 |
| 244-C10 LNP | 87 |
| 245-C10 LNP | 91 |
| 246-C10 LNP | 94 |

As confirmed in the Table 5, it was confirmed that the lipid nanoparticles according to one example could encapsulate a drug with high efficiency.

Example 5. Confirmation of Intracellular Nucleic Acid Delivery Using Lipid Nanoparticles

Example 5-1. Nucleic Acid Delivery Effect According to Types of Ionizable Lipids Comprised in LNP One day prior to transfection of LNP according to one example into cells, HeLa cells (Korea Cell Line Bank) were aliquoted at 0.01×10.sup.6 cells/well in a white plate (96 well) and were cultured under the condition of 37° C., 0.5-3% CO.sub.2 in DMEM media (SH30022, Hyclone, USA). After stirring LNPs (241-C10 LNP to 246-C10 LNP comprising 1.5 mol % of lipid-PEG) in which mRNA (luc mRNA; SEQ ID NO: 1) encoding a luciferase gene with ApoE30.1 ug/ml by pipetting and then incubating at a room temperature for 10 minutes, they were treated (100 ng/well based on the mRNA comprised in the lipid nanoparticles) in HeLa cells. ApoE3 binds to the LNP surface and plays a role in allowing LNP to enter the cell through endocytosis through an LDL receptor expressed on the cell surface.

Figure 4A:
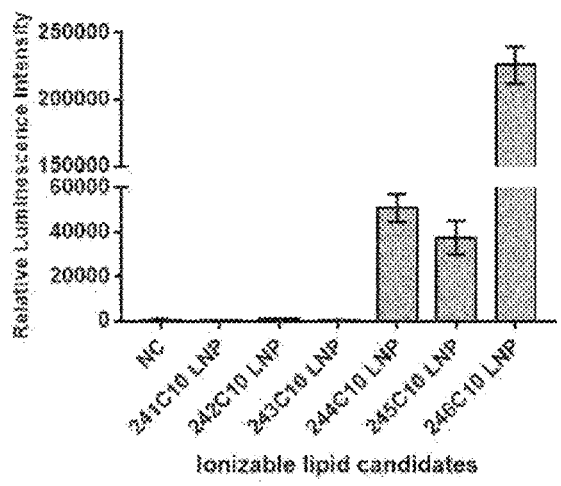
FIG. 4a and FIG. 4b are results showing the intracellular gene delivery efficiency of each nanoparticle. Specifically.

In 24 hours, after treating 1000/well of Bright-Glo™ Luciferase Assay solution (promega, USA) each and leaving them at a room temperature for 10 minutes, the luminescence intensity was measured for the dissolved cells using Infinite M200 luminescence measuring device (Tecan, USA), and the result was shown in FIG. 4a. As shown in FIG. 4a, 244-C10 LNP, 245-C10 LNP, and 246-C10 LNP having a pKa range of 6.0 to 7.0 showed strong luminescence intensity, and among them, 246-C10 LNP had the highest luminescence intensity, and therefore, it could be seen that 246-C10 LNP had the highest intracellular drug delivery efficiency.

Example 5-2. Confirmation of Nucleic Acid Delivery in Hepatocytes

The luminescence intensity was measured by delivering luc mRNA into hepatocytes using 246-C10 lipid nanoparticle prepared in Example 2-2, thereby confirming expression of the gene.

Specifically, after combining 246-C10 LNP (comprising 1.5 mol % of lipid-PEG) in which luc mRNA (SEQ ID NO: 1) was encapsulated with ApoE3 5 ug/ml, the LNP was treated into a hepatocyte cell line (Nexel, Korea) aliquoted at 1×10$^5$ cells/well at 0.2 ug/well, 0.5 ug/well, or 1 ug/well based on the mRNA concentration comprised in the nanoparticle. In 6 hours, Bright-Glo™ Luciferase Assay solution (promega, USA) of 100 μl/well was treated and left at a room temperature for 10 minutes, and then the luminescence intensity was measured for the dissolved cells using Infinite M200 luminescence measuring device (Tecan, US) and the result was shown in FIG. 4b.

Figure 4B:
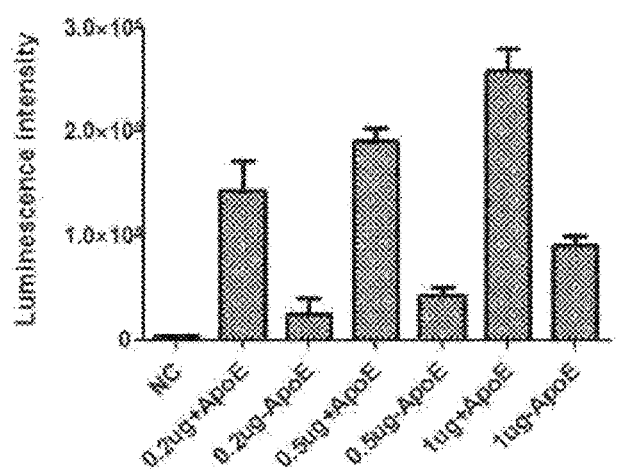

As confirmed in FIG. 4b, it was confirmed that the lipid nanoparticle according to one example was easy to introduce into cells through binding to ApoE3, increased the amount of drug (nucleic acid) delivery in a concentration-dependent manner, and could deliver the drug to hepatocytes with high efficiency.

Example 6. Confirmation of In Vivo Expression Using Lipid Nanoparticles

As confirmed in the Example 5-1, in vivo drug delivery efficiency and biodistribution of 244-C10 LNP to 246-C10 LNP showing an excellent gene expression effect (gene delivery effect) in vitro were to be confirmed in the present example.

244-C10 to 246-C10 LNP (comprising 1.5 mol % of lipid-PEG) in which luc mRNA (SEQ ID NO: 1) was encapsulated by the method of Example 2-2 were prepared, and each nanoparticle was dialyzed in PBS for 16 hours to remove ethanol. In 3 hours after intravenously (i.v) injecting the lipid nanoparticle in which mRNA was encapsulated into C57BL/6 Female 7-week-old mice (Orient Bio) in an amount of 0.1 mg/kg based on the mRNA comprised in the lipid nanoparticle, luciferin 0.25 mg/kg was intraperitoneally administered and the bioluminescence was confirmed through IVIS (PerkinElmer, USA) equipment, and the result was shown in FIG. 5a.

Figure 5A:
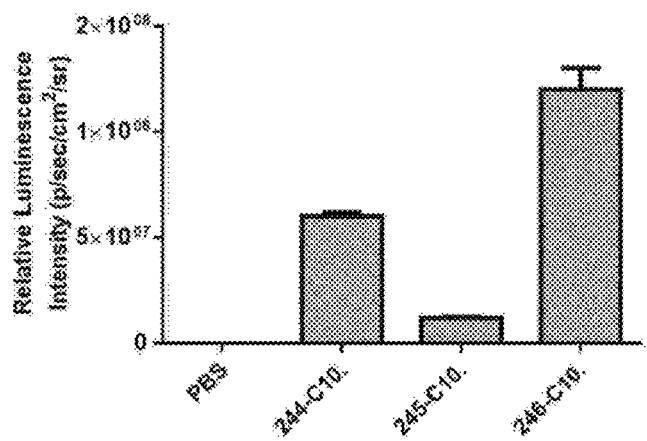
FIG. 5a shows in vivo drug delivery distribution in a mouse to which 244-C10 LNP to 246-C10 LNP with Luc mRNA encapsulated is administered.
Figure 5B:
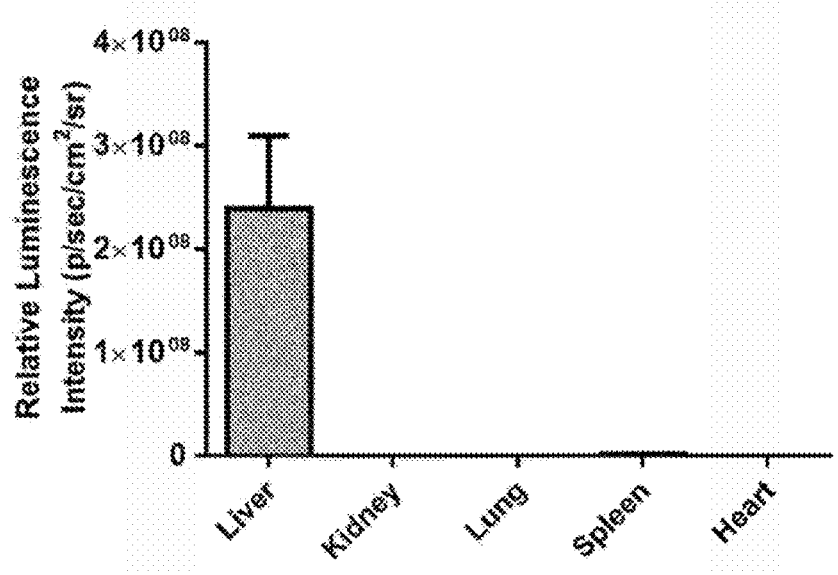
FIG. 5b shows drug delivery distribution to each organ of the mouse removed from the mouse in which 246-C10 LNP with Luc mRNA encapsulated is administered.

Mice in which luc mRNA-encapsulated 246-C10 LNP was administered were sacrificed and organs were removed, and the biodistribution of the lipid nanoparticle was confirmed in each organ through IVIS equipment and the result was shown in FIG. 5b.

As shown in FIG. 5a, mice in which luc mRNA-encapsulated 244-C10 LNP to 246-C10 LNP were administered showed high luminescence intensity, and this corresponds to the result of the Example 5-1. In particular, as shown in FIG. 5a and FIG. 5b, through systemic imaging and ex vivo organ imaging, it was confirmed that luc mRNA-encapsulated 246-C10 LNP showed high luminescence intensity specifically to liver, and thereby it could be confirmed that the lipid nanoparticle according to one example showed high biodistribution to the liver.

Example 7. Confirmation of Composition Ratio of Lipid Nanoparticles Optimal for Nucleic Acid Delivery In the present example, the composition ratio of the lipid nanoparticle with the most excellent drug delivery efficiency specifically to liver in vivo was to be confirmed.

In the preparation of the lipid nanoparticle, the lipid nanoparticle (246-C10 LNP) in which luc mRNA (SEQ ID NO: 1) was encapsulated was prepared by the method of Example 2-2 by mixing lipid-PEG (C16-PEG2000 ceramide) at 1.0 to 2.5 mol %. The weight ratio of the ionizable lipid:mRNA comprised in the lipid nanoparticle was 10:1, and the molar ratio of the ionizable lipid (246-C10):phospholipid (DOPE):cholesterol:lipid-PEG (C16-PEG2000 ceramide) comprised in the LNP was 26.5:20:52.5 to 51:1.0 to 2.5 (adjusting the content of cholesterol and lipid-PEG so that the total sum of the molar ratio is 100).

Figure 6:
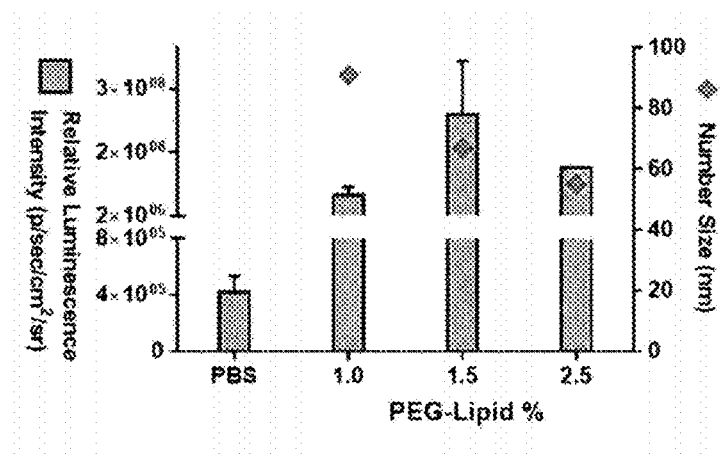
FIG. 6 shows the drug delivery efficiency of the lipid nanoparticle and the size of the nanoparticle, depending on the content of lipid-PEG comprised in the lipid nanoparticle in the mouse in which 246-C10 LNP comprising lipid-PEG in an amount of 1.0 to 2.5 mol % is administered.

For the 246-C10 LNP in which lipid-PEG was contained at 1.0 mol %, 1.5 mol %, or 2.5 mol % and luc mRNA was encapsulated, similarly to the method of Example 6, in 3 hours after mRNA-encapsulated lipid nanoparticle was intravenously (i.v) injected to C57BL/6 Female 7-week-old mice (Orient Bio) at a dose of 0.1 mg/kg based on the luc mRNA contained in the lipid nanoparticle, luciferin 0.25 mg/kg was intraperitoneally administered through IVIS (PerkinElmer, USA) equipment to confirm bioluminescence, and the result was shown in FIG. 6, and the size of the lipid nanoparticles according to the lipid-PEG content was measured as same as the method of Example 4-1 and was described in Table 6 and FIG. 6 below.

TABLE 6

| Lipid-PEG content comprised in LNP | Diameter (nm) |
|---|---|
| 1.0 mol % | 90 |
| 1.5 mol % | 67 |
| 2.5 mol % | 55 |

As shown in FIG. 6, it could be confirmed that the group in which the lipid nanoparticle according to one example was administered had excellent drug delivery efficiency to the liver, and the LNP size comprising lipid-PEG of 1.5 mol % was about 70 nm.

Example 8. Confirmation of Hepatocyte-Specific Drug Delivery Effect

Example 8-1. Confirmation of Knockout Effect of FVII Using Lipid Nanoparticles FVII is expressed specifically in hepatocytes and therefore, in the present example, the hepatocyte targetability of the lipid nanoparticles according to one example was to be confirmed through an FVII (Factor VII) knockout effect using siFVII.

Figure 7:
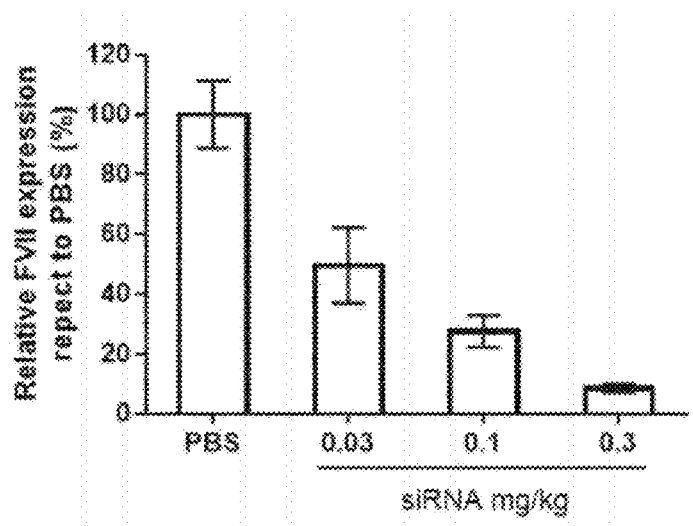
FIG. 7 shows the result of confirming the hepatocyte targeting possibility according to the concentration of siFVII administered as encapsulated in the lipid nanoparticle through the expression of FVII.

So that a concentration based on the concentration of siRNA comprised in the lipid nanoparticle was 0.03 mg/kg, 0.1 mg/kg, or 0.3 mg/kg, in 3 days after the 246-C10 lipid nanoparticle (comprising lipid-PEG of 1.5 mol %) in which FVII target siRNA (SEQ ID NOs: 2 and 3) was encapsulated, prepared in Example 2-2 was intravenously injected to C57BL/6 female 7-week-old 20 g mice, blood was collected through tail veins, and blood analysis was performed according to the protocol of the coaset FVII assay kit, and a standard curve was drawn with blood of mice administered with PBS and the FVII expression was measured and the result was shown in FIG. 7. As shown in FIG. 7, as FVII expression was inhibited in vivo dependently on the siRNA concentration encapsulated in the 246-C10 lipid nanoparticle, it was confirmed that the lipid nanoparticle according to one example could deliver a nucleic acid to hepatocytes as a target.

Example 8-2. Drug Delivery Effect to Hepatocytes According to Lipid-PEG Content

The lipid nanoparticle (246-C10 LNP) in which siFVII (SEQ ID Nos: 2 and 3) was encapsulated by the method of Example 2-2, by modifying the content of lipid-PEG comprised in the lipid nanoparticle to 0.5 to 5.0 mol %, was prepared. The weight ratio of the ionizable lipid:siRNA comprised in the lipid nanoparticle was 7.5:1, and the molar ratio of the ionizable lipid (246-C10):phospholipid (DSPC):cholesterol:lipid-PEG (C16-PEG2000 ceramide) comprised in the LNP was 42.5:13:44 to 39.5:0.5 to 5.0 (adjusting the content of cholesterol and lipid-PEG so that the total sum of the molar ratio is 100).

The diameter and polydispersity index of the lipid nanoparticles prepared above were measured as same as the method of Example 4-1, and were shown in Table 7 and FIG. 8 (left table) below.

TABLE 7

| Lipid-PEG (%) | Average diameter (nm) | PDI |
|---|---|---|
| 0.5 | 120 | 0.018 |
| 1 | 78 | 0.106 |
| 1.5 | 52 | 0.159 |
| 3 | 42 | 0.152 |
| 5 | 37 | 0.226 |

Figure 8:
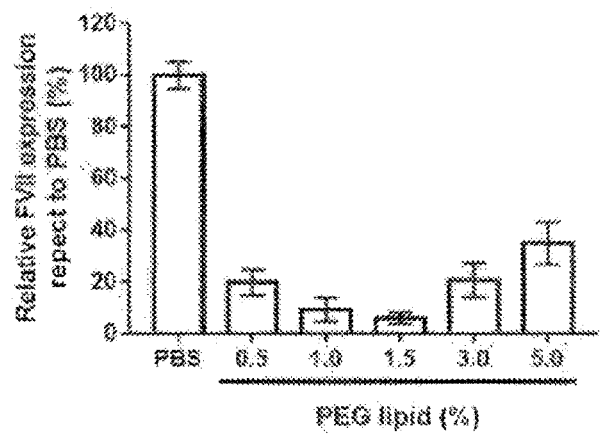
FIG. 8 shows the size of the lipid nanoparticle and PDI value of the lipid nanoparticle according to the content of the lipid-PEG comprised in the lipid nanoparticle (left table), and shows the result of confirming the in vivo drug delivery efficiency to the hepatocyte through the expression of FVII (right graph).

So that a concentration based on the concentration of siRNA comprised in the lipid nanoparticle was 0.2 mg/kg, in 3 days after the lipid nanoparticle (comprising lipid-PEG of 0.5 to 5 mol %) in which siFVII was encapsulated was intravenously injected to C57BL/6 female 7-week-old 20 g mice, blood was collected through tail veins, and similarly to the method of Example 8-1, using coaset FVII assay kit, the FVII expression was measured and the result was shown in FIG. 8 (right graph). As shown in FIG. 8, it was confirmed that when the lipid nanoparticle according to one example was administered, the FVII expression in vivo was reduced, and when the lipid nanoparticle having a lipid-PEG content of 0.5 to 5.0 mol % was administered, the FVII expression was excellently inhibited.

Example 9. LSEC-Specific Drug Delivery Effect

As FVIII is specifically expressed in LSEC (liver sinusoidal endothelial cells), in the present example, the LSEC targetability of the lipid nanoparticle according to one example was to be confirmed through a knockout effect of FVIII (Factor VIII) using siFVIII, and the drug delivery effect according to the lipid-PEG content was examined.

By modifying the content of lipid-PEG comprised in the lipid nanoparticle to 0.5 to 5.0 mol %, lipid nanoparticles (246-C10 LNP) in which siFVIII (SEQ ID Nos: 4 to 11) was encapsulated were prepared by the method of Example 2. The weight ratio of the ionizable lipid:siRNA comprised in the lipid nanoparticle was 7.5:1, and the ionizable lipid (246-C10):phospholipid (DSPC):cholesterol:lipid-PEG (C16-PEG2000 ceramide) comprised in the LNP=42.5:13:44 to 39.5:0.5 to 5.0 (adjusting the content of cholesterol and lipid-PEG so that the total sum of the molar ratio is 100).

The diameter and PDI of the lipid nanoparticles prepared above were measured by the same method of Example 4-1, and were shown in Table 8 and FIG. 9 (left table) below.

TABLE 8

| Lipid-PEG (%) | Average diameter (nm) | PDI |
|---|---|---|
| 0.5 | 166 | 0.018 |
| 1 | 87 | 0.106 |
| 1.5 | 78 | 0.159 |
| 3 | 42 | 0.152 |
| 5 | 35.6 | 0.226 |

Figure 9:
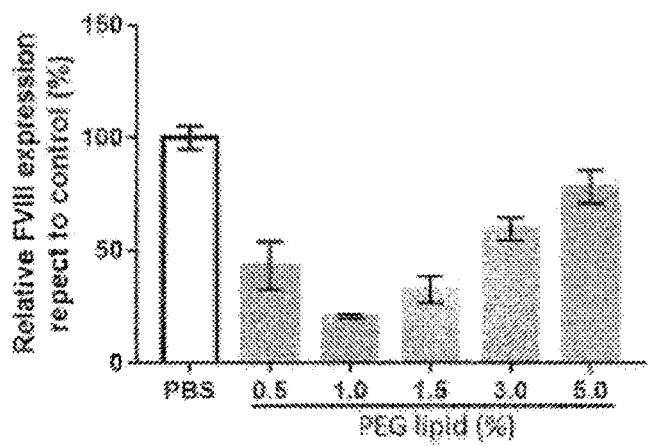
FIG. 9 shows the size of the lipid nanoparticle and PDI value of the lipid nanoparticle according to the content of the lipid-PEG comprised in the lipid nanoparticle (left table), and shows the result of confirming the in vivo drug delivery efficiency to the LSEC through the expression of FVIII (right graph).

So that a concentration based on the concentration of siRNA comprised in the lipid nanoparticle was 0.5 mg/kg, in 2 days after the lipid nanoparticle (comprising lipid-PEG of 0.5 to 5 mol %) in which siFVIII was encapsulated was intravenously injected to C57BL/6 female 7-week-old 20 g mice, blood was collected through tail veins, and similarly to the method of Example 8-1, using coaset FVII assay kit, the FVIII expression was measured and the result was shown in FIG. 9 (right graph). As shown in FIG. 9, it was confirmed that when the lipid nanoparticle according to one example was administered, the FVIII expression in vivo was reduced, and the lipid nanoparticle according to one example could target the LSEC, and when the lipid nanoparticle having a lipid-PEG content of 0.5 to 5.0 mol % was administered, the FVIII expression was excellently inhibited.

Example 10. Drug Delivery Effect According to Types of Lipid-PEG Conjugates

Lipid nanoparticles (comprising a lipid-PEG conjugate of 0.25 to 10.0 mol %) comprising a ceramide-PEG conjugate (C16-PEG 2000 ceramide; Avanti, US) or PEG-DSPE (Avanti, US) as a lipid-PEG conjugate were prepared similarly to the method of Example 2-2.

The weight ratio of the ionizable lipid:siRNA (siLuc) comprised in the lipid nanoparticle was 7.5:1, and the molar ratio of the ionizable lipid (2464-C10):phospholipid (DSPC):cholesterol:lipid-PEG (ceramide-PEG or PEG-DSPE) comprised in the LNP was 42.5:13:44.25 to 34.5:0.25 to 10 (adjusting the content of cholesterol and lipid-PEG so that the total sum of the molar ratio is 100). The sequence of the used siLuc (siRNA targeting a luciferase gene; SEQ ID Nos: 12 and 13) was described in the Example 2-2.

One day prior to transfection of LNP according to one example into cells, HeLa cells (Korea Cell Line Bank) were aliquoted at $0.01 \times 10^6$ cells/well in a white plate (96 well) and were cultured under the condition of 37° C., 0.5-3% $CO_2$ in DMEM media (SH30022, Hyclone, USA). In 24 hours after treating the lipid nanoparticle in which siLuc was encapsulated to the HeLa-Luc cell line at 10 nM based on the siRNA concentration, Bright-Glo™ Luciferase Assay solution (promega, USA) was treated by 100 111/well each and was left at a room temperature for 10 minutes, and then for the dissolved cells, the luminescence intensity was measured using Infinite M200 luminescence measuring device (Tecan, USA), and the result was shown in FIG. 10. The measured result was represented by mean±SD. The result value was statistically verified by the T-test method, and a case of p<0.05 or more was defined as statistically significant.

Figure 10:
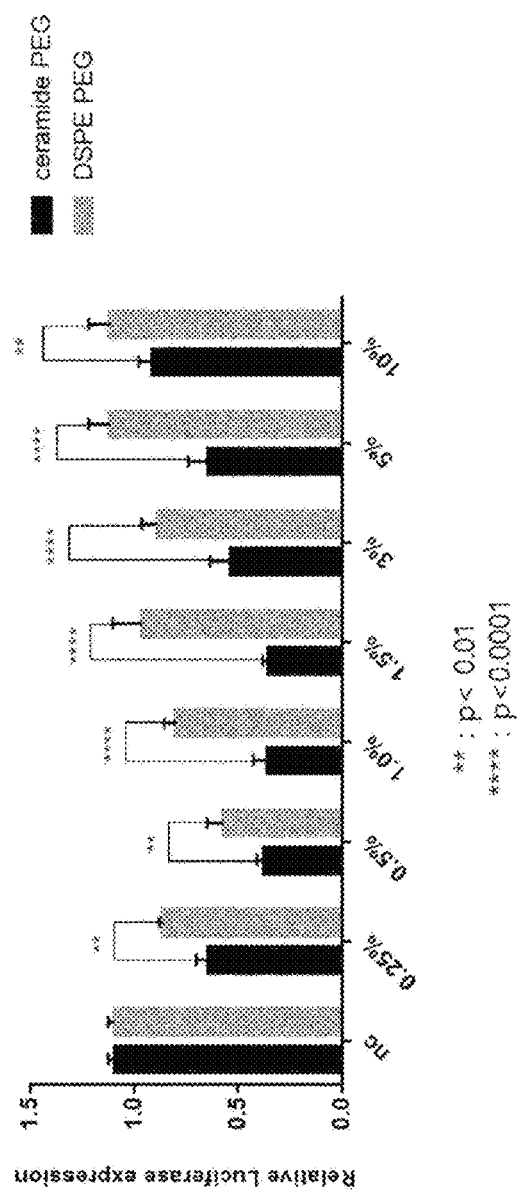
FIG. 10 shows the result of measuring the intracellular siRNA delivery efficiency of the lipid nanoparticle comprising ceramide-PEG or DSPE-PEG.

As shown in FIG. 10, the lipid nanoparticle according to one example had an excellent nucleic acid delivery effect to cells, and in particular, in case of comprising the ceramide-PEG conjugate as a lipid-PEG conjugate, the nucleic acid delivery effect was excellent.

The invention claimed is:

1. An ionizable lipid compound represented by the following formula:

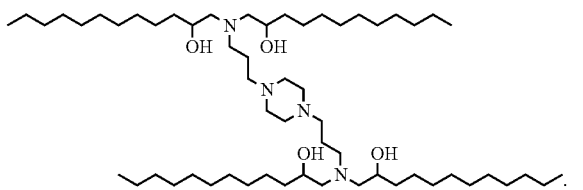 [SMILES: CCCCCCCCCCC(O)CN(CCCN1CCN(CCCN(CC(O)CCCCCCCCCC)CC(O)CCCCCCCCCC)CC1)CC(O)CCCCCCCCCC]

2. A lipid nanoparticle of claim 1 comprising the compound of claim 1.

3. The lipid nanoparticle of claim 2, further comprising a phospholipid, cholesterol, and a lipid-PEG (polyethyleneglycol) conjugate.

4. The lipid nanoparticle according to claim 3, wherein the phospholipid is at least one selected from the group consisting of DOPE, DSPC, POPC, EPC, DOPC, DPPC, DOPG, DPPG, DSPE, Phosphatidylethanolamine, dipalmitoylphosphatidylethanolamine, 1,2-dioleoyl-sn-glycero-3-phosphoethanolamine, POPE, POPC, DOPS, and 1,2-dioleoyl-sn-glycero-3-[phospho-L-serine].

5. The lipid nanoparticle according to claim 3, wherein the lipid in the lipid-PEG conjugate is at least one selected from the group consisting of ceramide, dimyristoylglycerol (DMG), succinoyl-diacylglycerol (s-DAG), di stearoylphosphatidylcholine (DSPC), distearoylphosphatidylethanolamine (DSPE), and cholesterol.

6. The lipid nanoparticle according to claim 3, wherein the lipid-PEG conjugate is comprised in 0.25 to 10 mol %.

7. The lipid nanoparticle according to claim 3, which comprises the ionizable lipid, the phospholipid, the cholesterol, and the lipid-PEG conjugate at a molar ratio of 20 to 50:10 to 30:30 to 60:0.25 to 10.

8. The lipid nanoparticle according to claim 3, wherein the lipid nanoparticle has a pKa of 6.0 to 7.0.

9. The lipid nanoparticle according to claim 3, wherein the lipid nanoparticle specifically targets liver tissue.

10. The lipid nanoparticle according to claim 3, wherein the lipid nanoparticle targets a hepatocyte.

11. The lipid nanoparticle according to claim 3, wherein the lipid nanoparticle targets an LSEC (liver sinusoidal endothelial cell).

12. A method of delivering a drug, comprising administering a composition comprising (1) the lipid nanoparticle according to of claim 3; and (2) the drug, wherein the drug is an anionic drug, a nucleic acid or a combination thereof, to a subject in need of delivering the drug.

13. The method according to claim 12, wherein the anionic drug, nucleic acid or combination thereof is encapsulated inside of the lipid nanoparticle.

14. The method according to claim 12, wherein the lipid nanoparticle has an average diameter of nm to 150 nm.

15. The method according to claim 12, wherein the anionic drug is one or more kinds selected from the group consisting of a peptide, a drug protein, a protein-nucleic acid structure, and an anionic biopolymer-drug conjugate.

16. The method according to claim 12, wherein the nucleic acid is one or more kinds selected from the group consisting of small interfering ribonucleic acid (siRNA), ribosome ribonucleic acid (rRNA), ribonucleic acid (RNA), deoxyribonucleic acid (DNA), complementary deoxyribonucleic acid (cDNA), aptamer, messenger ribonucleic acid (mRNA), transfer ribonucleic acid (tRNA), antisense oligonucleotide, shRNA, miRNA, ribozyme, PNA and DNAzyme.

17. A method for preventing or treating liver disease comprising administering a composition comprising (1) the lipid nanoparticle according to claim 1; and (2) an anionic drug, a nucleic acid or a combination thereof, to a subject in need of preventing or treating the liver disease.

18. The method according to claim 17, wherein the liver disease is one or more kinds selected from the group consisting of ATTR amyloidosis, hypercholesterolemia, hepatitis B virus infection, acute liver failure, cirrhosis, and liver fibrosis.

19. The method according to claim 17, wherein the lipid nanoparticle has an average diameter of 30 nm to 150 nm.

* * * * *

SEQUENCE LISTING

```
Sequence total quantity: 13
SEQ ID NO: 1              moltype = RNA   length = 1653
FEATURE                   Location/Qualifiers
misc_feature              1..1653
                          note = Synthetic_luciferase mRNA
source                    1..1653
                          mol_type = other RNA
                          organism = synthetic construct
SEQUENCE: 1
atggaagacg ccaaaaacat aaagaaaggc ccggcgccat tctatccgct ggaagatgga   60
accgctggag agcaactgca taaggctatg aagagatacg ccctggttcc tggaacaatt  120
gcttttacag atgcacatat cgaggtggac atcacttacg ctgagtactt cgaaatgtcc  180
gttcggttgg cagaagctat gaaacgatat gggctgaata caaatcacag aatcgtcgta  240
tgcagtgaaa actctcttca attctttatg ccggtgttgg gcgcgttatt tatcggagtt  300
gcagttgcgc ccgcgaacga catttataat gaacgttgtc tcaacagtat gggcatt     360
tcgcagccta ccgtggtgtt cgtttccaaa aaggggttgc aaaaaatttt gaacgtgcaa  420
aaaaagctcc caatcatcca aaaaattatt atcatggatt ctaaaacgga ttaccaggga  480
tttcagtcga tgtacacgtt cgtcacatct catctacctc ccggttttaa tgaatacgat  540
tttgtgccag agtccttcga tagggacaag acaattgcac tgatcatgaa ctcctctgga  600
tctactggtc tgcctaaagg tgtcgctctg cctcatagaa ctgcctgcgt gagattctcg  660
catgccagag atcctatttt tggcaatcaa atcattccgg atactgcgat tttaagtgtt  720
gttccattcc atcacggttt tggaatgttt actacactcg gatatttgat atgtggattt  780
cgagtcgtct taatgtatag atttgaagaa gagctgtttc tgaggagcct tcaggattac  840
aagattcaaa gtgcgctgct ggtgccaacc ctattctcct tcttcgccaa agcactctg   900
attgacaaat acgatttatc taatttacac gaaattgctt ctggtggcgc tcccctctct  960
aaggaagtcg gggaagcggt tgccaagagg ttccatctgc caggtatcag gcaaggatat 1020
gggctcactg agactacatc agctattctg attacacccg aggggggatga taaaccgggc 1080
gcggtcggta aagttgttcc atttttgaa gcgaaggttg tggatctgga taccgggaaa 1140
acgctgggcg ttaatcaaag aggcgaactg tgtgtgagag tcctatgat tatgtccggt  1200
tatgtaaaca atccggaagc gaccaacgcc ttgattgaca aggatggatg gctacattct 1260
ggagacatag cttactggga cgaagacgaa cacttcttca tcgttgaccg cctgaagtct 1320
ctgattaagt acaaaggcta tcaggtggct cccgctgaat tggaatccat cttgctccaa 1380
cacccccaaca tcttcgacgc aggtgtcgca ggtcttcccg acgatgacgc cggtgaactt 1440
cccgccgccg ttgttgtttt ggagcacgga aagacgatga cggaaaaaga gatcgtggat 1500
tacgtcgcca gtcaagtaac aaccgcgaaa aagttgcgcg gaggagttgt gtttgtggac 1560
gaagtaccga aaggtcttac cggaaaactc gacgcaagaa aaatcagaga gatcctcata 1620
aaggccaaga agggcggaaa gatcgccgtg taa                              1653

SEQ ID NO: 2              moltype = RNA   length = 21
FEATURE                   Location/Qualifiers
modified_base             20..21
                          mod_base = OTHER
                          note = deoxyribonucleotides: thymine
misc_feature              1..21
                          note = Synthetic_FVII target siRNA_sense
source                    1..21
                          mol_type = other RNA
                          organism = synthetic construct
SEQUENCE: 2
ggatcatctc aagtcttact t                                              21

SEQ ID NO: 3              moltype = RNA   length = 21
FEATURE                   Location/Qualifiers
modified_base             20..21
                          mod_base = OTHER
                          note = deoxyribonucleotides: thymine
misc_feature              1..21
                          note = Synthetic_FVII target siRNA_antisense
source                    1..21
                          mol_type = other RNA
                          organism = synthetic construct
SEQUENCE: 3
gtaagacttg agatgatcct t                                              21

SEQ ID NO: 4              moltype = RNA   length = 21
FEATURE                   Location/Qualifiers
modified_base             20..21
                          mod_base = OTHER
                          note = deoxyribonucleotides: thymine
misc_feature              1..21
                          note = Synthetic_FVIII target siRNA_sense_1
source                    1..21
                          mol_type = other RNA
                          organism = synthetic construct
SEQUENCE: 4
cttatatcgt ggagaattat t                                              21

SEQ ID NO: 5              moltype = RNA   length = 21
```

```
FEATURE              Location/Qualifiers
modified_base        20..21
                     mod_base = OTHER
                     note = deoxyribonucleotides: thymine
misc_feature         1..21
                     note = Synthetic_FVIII target siRNA_antisense_1
source               1..21
                     mol_type = other RNA
                     organism = synthetic construct
SEQUENCE: 5
taattctcca cgatataagt t                                              21

SEQ ID NO: 6         moltype = RNA   length = 21
FEATURE              Location/Qualifiers
modified_base        20..21
                     mod_base = OTHER
                     note = deoxyribonucleotides: thymine
misc_feature         1..21
                     note = Synthetic_FVIII target siRNA_sense_2
source               1..21
                     mol_type = other RNA
                     organism = synthetic construct
SEQUENCE: 6
tcaaaggatt cgatggtatt t                                              21

SEQ ID NO: 7         moltype = RNA   length = 21
FEATURE              Location/Qualifiers
modified_base        20..21
                     mod_base = OTHER
                     note = deoxyribonucleotides: thymine
misc_feature         1..21
                     note = Synthetic_FVIII target siRNA_antisense_2
source               1..21
                     mol_type = other RNA
                     organism = synthetic construct
SEQUENCE: 7
ataccatcga atcctttgat t                                              21

SEQ ID NO: 8         moltype = RNA   length = 21
FEATURE              Location/Qualifiers
modified_base        20..21
                     mod_base = OTHER
                     note = deoxyribonucleotides: thymine
misc_feature         1..21
                     note = Synthetic_FVIII target siRNA_sense_3
source               1..21
                     mol_type = other RNA
                     organism = synthetic construct
SEQUENCE: 8
caagagcact agtgattatt t                                              21

SEQ ID NO: 9         moltype = RNA   length = 21
FEATURE              Location/Qualifiers
modified_base        20..21
                     mod_base = OTHER
                     note = deoxyribonucleotides: thymine
misc_feature         1..21
                     note = Synthetic_FVIII target siRNA_antisense_3
source               1..21
                     mol_type = other RNA
                     organism = synthetic construct
SEQUENCE: 9
ataatcacta gtgctcttgt t                                              21

SEQ ID NO: 10        moltype = RNA   length = 21
FEATURE              Location/Qualifiers
modified_base        20..21
                     mod_base = OTHER
                     note = deoxyribonucleotides: thymine
misc_feature         1..21
                     note = Synthetic_FVIII target siRNA_sense_4
source               1..21
                     mol_type = other RNA
                     organism = synthetic construct
SEQUENCE: 10
gggcaccact cctgaaatat t                                              21

SEQ ID NO: 11        moltype = RNA   length = 21
FEATURE              Location/Qualifiers
```

```
                        -continued modified_base           20..21
                        mod_base = OTHER
                        note = deoxyribonucleotides: thymine
misc_feature            1..21
                        note = Synthetic_FVIII target siRNA_antisense_4
source                  1..21
                        mol_type = other RNA
                        organism = synthetic construct
SEQUENCE: 11
tatttcagga gtggtgccct t                                              21

SEQ ID NO: 12           moltype = RNA   length = 21
FEATURE                 Location/Qualifiers
modified_base           20..21
                        mod_base = OTHER
                        note = deoxyribonucleotides: thymine
misc_feature            1..21
                        note = Synthetic_siFluc_sense
source                  1..21
                        mol_type = other RNA
                        organism = synthetic construct
SEQUENCE: 12
aacgctgggc gttaatcaat t                                              21

SEQ ID NO: 13           moltype = RNA   length = 21
FEATURE                 Location/Qualifiers
misc_feature            1..21
                        note = Synthetic_siFluc_antisense
source                  1..21
                        mol_type = other RNA
                        organism = synthetic construct
modified_base           20..21
                        mod_base = OTHER
                        note = deoxyribonucleotides: thymine
SEQUENCE: 13
ttgattaacg cccagcgttt t                                              21
```